(12) United States Patent
McMillan

(10) Patent No.: US 12,396,648 B1
(45) Date of Patent: Aug. 26, 2025

(54) WEARABLE DEVICE WITH LIGHT SOURCE AND OPTICAL SENSOR

(71) Applicant: ROCKLEY PHOTONICS LIMITED, Altrincham (GB)

(72) Inventor: James McMillan, Santa Monica, CA (US)

(73) Assignee: Rockley Photonics Limited, Altrincham (GB)

( * ) Notice: Subject to any disclaimer, the term of this patent is extended or adjusted under 35 U.S.C. 154(b) by 0 days.

(21) Appl. No.: 18/984,845

(22) Filed: Dec. 17, 2024

Related U.S. Application Data

(60) Provisional application No. 63/726,157, filed on Nov. 27, 2024.

(51) Int. Cl.
*A61B 5/02* (2006.01)
*A61B 5/021* (2006.01)
*A61B 5/026* (2006.01)
*A61B 5/0295* (2006.01)

(52) U.S. Cl.
CPC ........ *A61B 5/0295* (2013.01); *A61B 5/02141* (2013.01); *A61B 5/0261* (2013.01)

(58) Field of Classification Search
CPC .............. A61B 5/0261; A61B 5/02007; A61B 5/02416; A61B 5/681; A61B 5/6801; A61B 5/02028; A61B 5/02427; A61B 5/0295; A61B 5/7264; A61B 5/6802; A61B 5/0082; A61B 5/02158; A61B 5/02438; A61B 5/026; A61B 5/0059; A61B 2560/04; A61B 2560/0462; A61B 2562/0238; G02B 27/48; G02B 2006/12121; G02B 6/12004; G02B 27/0172

See application file for complete search history.

(56) References Cited

U.S. PATENT DOCUMENTS

| 4,674,011 A | 6/1987 | Patton et al. |
| 5,243,983 A | 9/1993 | Tarr et al. |
| 5,497,769 A | 3/1996 | Gratton et al. |

(Continued)

FOREIGN PATENT DOCUMENTS

| CA | 2 861 089 C | 1/2021 |
| CN | 108709847 A | 10/2018 |

(Continued)

OTHER PUBLICATIONS

European Patent Office Communication pursuant to Article 94(3) EPC, for Patent Application No. 22776935.3, dated Jun. 24, 2025, 7 pages.

(Continued)

*Primary Examiner* — Deborah L Malamud
(74) *Attorney, Agent, or Firm* — Womble Bond Dickinson (US) LLP

(57) ABSTRACT

A wearable device with a light source and an optical sensor. In some embodiments, a system includes a wearable device for being worn by a subject and for measuring a first biomarker of a blood vessel of the subject. The wearable device may include a first light source, and a plurality of optical detectors. The system may be configured: to perform a photoplethysmography measurement with each of the plurality of optical detectors, the first biomarker being a blood volume; or to perform a speckleplethysmography measurement with each of the plurality of optical detectors, the first biomarker being a blood flow velocity.

14 Claims, 10 Drawing Sheets

(56) References Cited

U.S. PATENT DOCUMENTS

| | | |
|---|---|---|
| 5,532,860 A | 7/1996 | Hershey et al. |
| 5,772,587 A | 6/1998 | Gratton et al. |
| 5,830,132 A | 11/1998 | Robinson |
| 6,154,259 A | 11/2000 | Hargis et al. |
| 6,243,601 B1 | 6/2001 | Wist |
| 6,246,892 B1 | 6/2001 | Chance |
| 6,256,016 B1 | 7/2001 | Piot et al. |
| 6,560,478 B1 | 5/2003 | Alfano et al. |
| 6,919,549 B2 | 7/2005 | Bamji et al. |
| 7,035,679 B2 | 4/2006 | Addison et al. |
| 7,113,817 B1 | 9/2006 | Winchester, Jr. et al. |
| 7,202,466 B2 | 4/2007 | Babayoff et al. |
| 7,250,317 B2 | 7/2007 | Heideman |
| 7,295,783 B2 | 11/2007 | Singh et al. |
| 7,375,812 B2 | 5/2008 | Atia et al. |
| 7,474,407 B2 | 1/2009 | Gutin |
| 7,505,128 B2 | 3/2009 | Zribi et al. |
| 7,616,984 B2 | 11/2009 | Barbour et al. |
| 7,761,126 B2 | 7/2010 | Gardner et al. |
| 7,865,225 B2 | 1/2011 | Kaltschmidt et al. |
| 7,922,664 B2 | 4/2011 | Elliott |
| 7,925,056 B2 | 4/2011 | Presura et al. |
| 8,237,927 B1 | 8/2012 | Reeve et al. |
| 8,277,384 B2 | 10/2012 | Fine |
| 8,313,439 B2 | 11/2012 | McCombie et al. |
| 8,343,062 B2 | 1/2013 | Fortin et al. |
| 8,343,063 B2 | 1/2013 | Borgos |
| 8,376,955 B2 | 2/2013 | Baker, Jr. |
| 8,398,556 B2 | 3/2013 | Sethi et al. |
| 8,868,149 B2 | 10/2014 | Eisen et al. |
| 8,920,332 B2 | 12/2014 | Hong et al. |
| 8,923,942 B2 | 12/2014 | Bernreuter |
| 8,945,017 B2 | 2/2015 | Venkatraman et al. |
| 8,948,832 B2 | 2/2015 | Hong et al. |
| 8,956,303 B2 | 2/2015 | Hong et al. |
| 8,998,815 B2 | 4/2015 | Venkatraman et al. |
| 9,005,129 B2 | 4/2015 | Venkatraman et al. |
| 9,113,794 B2 | 8/2015 | Hong et al. |
| 9,113,795 B2 | 8/2015 | Hong et al. |
| 9,149,216 B1 | 10/2015 | Eisen et al. |
| 9,155,480 B2 | 10/2015 | Thakor et al. |
| 9,226,673 B2 | 1/2016 | Ferguson, Jr. et al. |
| 9,237,855 B2 | 1/2016 | Hong et al. |
| 9,307,917 B2 | 4/2016 | Hong et al. |
| 9,494,567 B2 | 11/2016 | Islam |
| 9,687,162 B2 | 6/2017 | Vetter et al. |
| 9,704,050 B2 | 7/2017 | Lee et al. |
| 9,730,622 B2 | 8/2017 | Eisen et al. |
| 9,772,280 B2 | 9/2017 | Cerussi et al. |
| 9,804,027 B2 | 10/2017 | Fish et al. |
| 9,846,126 B2 | 12/2017 | Gunn, III et al. |
| 9,848,787 B2 | 12/2017 | White et al. |
| 9,851,298 B1 | 12/2017 | Isikman et al. |
| 9,877,681 B2 | 1/2018 | Silverman |
| 9,931,040 B2 | 4/2018 | Homyk et al. |
| 9,970,955 B1 | 5/2018 | Homyk et al. |
| 10,004,406 B2 | 6/2018 | Yuen et al. |
| 10,058,256 B2 | 8/2018 | Chen et al. |
| 10,178,959 B1 | 1/2019 | Homyk et al. |
| 10,178,973 B2 | 1/2019 | Venkatraman et al. |
| 10,194,808 B1 | 2/2019 | Thompson et al. |
| 10,206,576 B2 | 2/2019 | Shcherbakov et al. |
| 10,215,698 B2 | 2/2019 | Han et al. |
| 10,241,033 B2 | 3/2019 | Uematsu et al. |
| 10,271,740 B2 | 4/2019 | Ward et al. |
| 10,314,532 B2 | 6/2019 | Ward et al. |
| 10,326,035 B2 | 6/2019 | Lu et al. |
| 10,326,036 B2 | 6/2019 | Sweeney et al. |
| 10,349,847 B2 | 7/2019 | Kwon et al. |
| 10,352,768 B2 | 7/2019 | Simpkin et al. |
| 10,357,165 B2 | 7/2019 | Yoon |
| 10,420,498 B1 | 9/2019 | Horstmeyer et al. |
| 10,422,693 B2 | 9/2019 | Fish et al. |
| 10,451,537 B2 | 10/2019 | Nakaji |
| 10,463,286 B2 | 11/2019 | Schenkman et al. |
| 10,492,684 B2 | 12/2019 | Khachaturian et al. |
| 10,506,926 B2 | 12/2019 | Khachaturian et al. |
| 10,506,955 B2 | 12/2019 | Tholl et al. |
| 10,568,527 B2 | 2/2020 | Yoon et al. |
| 10,588,519 B2 | 3/2020 | Yuen et al. |
| 10,602,987 B2 | 3/2020 | Khachaturian et al. |
| 10,627,849 B1 | 4/2020 | Scofield et al. |
| 10,641,962 B1 | 5/2020 | Nykänen et al. |
| 10,643,903 B2 | 5/2020 | Drake et al. |
| 10,667,688 B2 | 6/2020 | Khachaturian et al. |
| 10,677,989 B2 | 6/2020 | Abediasl et al. |
| 10,681,259 B2 | 6/2020 | Ichiki et al. |
| 10,681,283 B2 | 6/2020 | Nakashima et al. |
| 10,694,997 B2 | 6/2020 | Kim et al. |
| 10,718,668 B2 | 7/2020 | Gu et al. |
| 10,722,177 B2 | 7/2020 | Homyk et al. |
| 10,739,256 B1 | 8/2020 | Rickman et al. |
| 10,750,956 B2 | 8/2020 | Zalevsky et al. |
| 10,775,239 B2 | 9/2020 | Lee et al. |
| 10,813,597 B2 | 10/2020 | Rice et al. |
| 10,820,858 B2 | 11/2020 | Yoon et al. |
| 10,842,422 B2 | 11/2020 | Yu et al. |
| 10,871,503 B1 | 12/2020 | Homyk et al. |
| 10,895,525 B2 | 1/2021 | Swanson |
| 10,966,616 B2 | 4/2021 | De Morree et al. |
| 10,973,422 B2 | 4/2021 | Pantelopoulos et al. |
| 11,022,751 B2 | 6/2021 | Bauters et al. |
| 11,045,103 B2 | 6/2021 | Shchekin et al. |
| 11,079,364 B2 | 8/2021 | Leger et al. |
| 11,096,601 B2 | 8/2021 | Hong et al. |
| 11,096,608 B2 | 8/2021 | Van Dorpe et al. |
| 11,129,544 B2 | 9/2021 | Zalevsky et al. |
| 11,202,582 B2 | 12/2021 | Verkruijsse et al. |
| 11,213,217 B2 | 1/2022 | Han et al. |
| 11,278,220 B2 | 3/2022 | Tucker et al. |
| 11,298,035 B2 | 4/2022 | Huijbregts et al. |
| 11,369,275 B2 | 6/2022 | Song et al. |
| 11,445,922 B2 | 9/2022 | Naima |
| 11,553,851 B2 | 1/2023 | Kim et al. |
| 11,583,185 B2 | 2/2023 | Homyk et al. |
| 11,666,238 B2 | 6/2023 | Rege et al. |
| 11,666,277 B2 | 6/2023 | Yoon et al. |
| 11,684,281 B2 | 6/2023 | Pantelopoulos et al. |
| 11,690,513 B2 | 7/2023 | Hu et al. |
| 11,696,693 B2 | 7/2023 | Wong |
| 11,709,120 B2 | 7/2023 | Rice et al. |
| 11,744,491 B2 | 9/2023 | Dunn et al. |
| 11,751,811 B2 | 9/2023 | Sun et al. |
| 11,759,116 B2 | 9/2023 | White et al. |
| 11,759,121 B2 | 9/2023 | Mccann et al. |
| 11,771,343 B2 | 10/2023 | Sacha |
| 11,800,990 B2 | 10/2023 | White et al. |
| 11,857,301 B1 | 1/2024 | Homyk et al. |
| 11,883,134 B2 | 1/2024 | Leabman |
| 11,890,081 B2 | 2/2024 | Jang |
| 11,980,451 B2 | 5/2024 | Albert |
| 12,109,006 B2 | 10/2024 | Dunn et al. |
| 2002/0195496 A1 | 12/2002 | Tsikos et al. |
| 2003/0052169 A1 | 3/2003 | Tsikos et al. |
| 2003/0137669 A1 | 7/2003 | Rollins et al. |
| 2005/0249509 A1 | 11/2005 | Nagarajan et al. |
| 2006/0124829 A1 | 6/2006 | Song et al. |
| 2006/0132790 A1 | 6/2006 | Gutin |
| 2006/0204175 A1 | 9/2006 | Laurent-Lund et al. |
| 2006/0247514 A1 | 11/2006 | Panasyuk et al. |
| 2007/0051601 A1 | 3/2007 | Wang et al. |
| 2007/0057182 A1 | 3/2007 | Feuerbaum |
| 2007/0093702 A1 | 4/2007 | Yu et al. |
| 2008/0097172 A1 | 4/2008 | Sawada et al. |
| 2008/0154126 A1 | 6/2008 | Culver et al. |
| 2008/0204752 A1 | 8/2008 | Dorvee et al. |
| 2008/0220512 A1 | 9/2008 | Koh et al. |
| 2008/0316567 A1 | 12/2008 | Grasser et al. |
| 2009/0177094 A1 | 7/2009 | Brown et al. |
| 2009/0202251 A1 | 8/2009 | Shibayama |
| 2009/0209834 A1 | 8/2009 | Fine |
| 2009/0284748 A1 | 11/2009 | Melman et al. |
| 2010/0004741 A1 | 1/2010 | Gupta et al. |
| 2010/0046234 A1 | 2/2010 | Abu-Ageel |

(56) References Cited

U.S. PATENT DOCUMENTS

| | | |
|---|---|---|
| 2010/0056928 A1 | 3/2010 | Zuzak et al. |
| 2010/0226646 A1 | 9/2010 | Chan et al. |
| 2011/0054277 A1 | 3/2011 | Pinter et al. |
| 2011/0082355 A1 | 4/2011 | Eisen et al. |
| 2011/0087108 A1 | 4/2011 | Onoe et al. |
| 2011/0196244 A1 | 8/2011 | Ribas Ripoll et al. |
| 2012/0130215 A1 | 5/2012 | Fine et al. |
| 2012/0232402 A1 | 9/2012 | MacFarlane et al. |
| 2013/0131475 A1 | 5/2013 | Eisen et al. |
| 2013/0190630 A1 | 7/2013 | Borgos |
| 2013/0204112 A1 | 8/2013 | White et al. |
| 2013/0278631 A1 | 10/2013 | Border et al. |
| 2014/0094666 A1 | 4/2014 | Fine |
| 2014/0118695 A1 | 5/2014 | Shimada et al. |
| 2014/0120319 A1 | 5/2014 | Joseph |
| 2014/0200423 A1 | 7/2014 | Eisen et al. |
| 2014/0313524 A1 | 10/2014 | Banyay et al. |
| 2014/0316286 A1 | 10/2014 | Addison et al. |
| 2014/0376001 A1 | 12/2014 | Swanson |
| 2015/0157224 A1 | 6/2015 | Carmon et al. |
| 2015/0196251 A1 | 7/2015 | Outwater et al. |
| 2015/0201854 A1 | 7/2015 | Hong et al. |
| 2015/0323311 A1 | 11/2015 | Muijs et al. |
| 2016/0058300 A1 | 3/2016 | Yoon et al. |
| 2016/0066790 A1 | 3/2016 | Shcherbakov et al. |
| 2016/0106327 A1 | 4/2016 | Yoon et al. |
| 2016/0157736 A1 | 6/2016 | Huang et al. |
| 2016/0161685 A1 | 6/2016 | Xu et al. |
| 2016/0183882 A1 | 6/2016 | Henley et al. |
| 2016/0195473 A1 | 7/2016 | Fujiwara et al. |
| 2016/0242647 A1 | 8/2016 | Ishii et al. |
| 2016/0266337 A1 | 9/2016 | Feng |
| 2016/0278676 A1 | 9/2016 | Eisen et al. |
| 2016/0282265 A1 | 9/2016 | Su et al. |
| 2016/0287107 A1 | 10/2016 | Szabados et al. |
| 2016/0360966 A1 | 12/2016 | Ishii et al. |
| 2017/0007138 A1 | 1/2017 | Kim et al. |
| 2017/0014037 A1 | 1/2017 | Coppola et al. |
| 2017/0065184 A1 | 3/2017 | Barak |
| 2017/0105618 A1 | 4/2017 | Schmoll et al. |
| 2017/0108439 A1 | 4/2017 | Stievater et al. |
| 2017/0138789 A1 | 5/2017 | Ivanov |
| 2017/0164878 A1 | 6/2017 | Connor |
| 2017/0188851 A1 | 7/2017 | LeBoeuf et al. |
| 2017/0231513 A1 | 8/2017 | Presura et al. |
| 2017/0315292 A1 | 11/2017 | Mullen et al. |
| 2018/0020962 A1 | 1/2018 | Yu et al. |
| 2018/0045566 A1 | 2/2018 | Fish et al. |
| 2018/0110423 A1 | 4/2018 | Presura et al. |
| 2018/0160913 A1 | 6/2018 | Fine |
| 2018/0168465 A1 | 6/2018 | Yamada et al. |
| 2018/0202927 A1 | 7/2018 | Isikman et al. |
| 2018/0228363 A1 | 8/2018 | Frisken et al. |
| 2018/0238794 A1 | 8/2018 | Kangas et al. |
| 2018/0263519 A1 | 9/2018 | Gu |
| 2018/0283950 A1 | 10/2018 | Ge et al. |
| 2018/0296168 A1 | 10/2018 | Rice et al. |
| 2019/0041736 A1 | 2/2019 | Grunnet-Jepsen et al. |
| 2019/0046056 A1 | 2/2019 | Khachaturian et al. |
| 2019/0053721 A1 | 2/2019 | Boas et al. |
| 2019/0094009 A1 | 3/2019 | Aizawa et al. |
| 2019/0094564 A1 | 3/2019 | Rivera et al. |
| 2019/0167118 A1 | 6/2019 | Vilenskii et al. |
| 2019/0175030 A1 | 6/2019 | Verkruijsse et al. |
| 2019/0336006 A1 | 11/2019 | Horstmeyer et al. |
| 2019/0343442 A1 | 11/2019 | Aung et al. |
| 2019/0343456 A1 | 11/2019 | Kahlert et al. |
| 2019/0369650 A1 | 12/2019 | Swanson et al. |
| 2019/0387972 A1 | 12/2019 | Hu et al. |
| 2019/0391243 A1 | 12/2019 | Nicolaescu |
| 2019/0391702 A1 | 12/2019 | Jo et al. |
| 2020/0003619 A1 | 1/2020 | Hu et al. |
| 2020/0011995 A1 | 1/2020 | Send et al. |
| 2020/0069225 A1 | 3/2020 | Vizbaras et al. |
| 2020/0100705 A1 | 4/2020 | Dellimore et al. |
| 2020/0143534 A1 | 5/2020 | Wright et al. |
| 2020/0158548 A1 | 5/2020 | Rice et al. |
| 2020/0196874 A1 | 6/2020 | Rozental et al. |
| 2020/0214602 A1 | 7/2020 | Narumi et al. |
| 2020/0237272 A1 | 7/2020 | Lin et al. |
| 2020/0249492 A1 | 8/2020 | Maes |
| 2020/0323440 A1 | 10/2020 | Vule et al. |
| 2020/0359948 A1 | 11/2020 | Dunn et al. |
| 2020/0397351 A1 | 12/2020 | Miyata |
| 2021/0000385 A1 | 1/2021 | Warren et al. |
| 2021/0022623 A1 | 1/2021 | Rice et al. |
| 2021/0028602 A1 | 1/2021 | Cao et al. |
| 2021/0161408 A1 | 6/2021 | Wakita |
| 2021/0186431 A1 | 6/2021 | Jung et al. |
| 2021/0267471 A1 | 9/2021 | Bonomi et al. |
| 2021/0321887 A1 | 10/2021 | Fukazawa et al. |
| 2021/0330202 A1 | 10/2021 | Konecky |
| 2021/0338083 A1 | 11/2021 | Sie et al. |
| 2021/0386310 A1 | 12/2021 | Hong et al. |
| 2021/0405518 A1 | 12/2021 | Lablans |
| 2022/0015649 A1 | 1/2022 | Ikuta et al. |
| 2022/0018762 A1 | 1/2022 | Ekin et al. |
| 2022/0019861 A1 | 1/2022 | Durr et al. |
| 2022/0039679 A1 | 2/2022 | Califa et al. |
| 2022/0061644 A1 | 3/2022 | Fontaine et al. |
| 2022/0104822 A1 | 4/2022 | Shelton, IV et al. |
| 2022/0117557 A1 | 4/2022 | Hsu et al. |
| 2022/0196557 A1 | 6/2022 | Zheng et al. |
| 2022/0211286 A1 | 7/2022 | Tank et al. |
| 2022/0265158 A1 | 8/2022 | Tokura |
| 2022/0370010 A1 | 11/2022 | Zilkie et al. |
| 2022/0413143 A1 | 12/2022 | Parsa et al. |
| 2023/0003938 A1 | 1/2023 | Zilkie et al. |
| 2023/0039055 A1 | 2/2023 | Gardner et al. |
| 2023/0048766 A1 | 2/2023 | Frey |
| 2023/0064006 A1 | 3/2023 | Kim et al. |
| 2023/0087295 A1 | 3/2023 | Dunn et al. |
| 2023/0148885 A1 | 5/2023 | Bechtel et al. |
| 2023/0148886 A1 | 5/2023 | Bechtel et al. |
| 2023/0164444 A1 | 5/2023 | Yang |
| 2023/0225643 A1 | 7/2023 | Scofield et al. |
| 2023/0277062 A1 | 9/2023 | Dalvi et al. |
| 2023/0277075 A1 | 9/2023 | Pantelopoulos et al. |
| 2023/0296510 A1 | 9/2023 | Xu |
| 2023/0320598 A1 | 10/2023 | Khine et al. |
| 2023/0347029 A1 | 11/2023 | Corso et al. |
| 2023/0375525 A1 | 11/2023 | Merritt et al. |
| 2023/0397818 A1 | 12/2023 | Newhouse et al. |
| 2023/0401747 A1 | 12/2023 | Dunn et al. |
| 2024/0032790 A1 | 2/2024 | Patel et al. |
| 2024/0041342 A1 | 2/2024 | Lai et al. |
| 2024/0074667 A1 | 3/2024 | Rick et al. |
| 2024/0108289 A1 | 4/2024 | Bechtel et al. |
| 2024/0115212 A1 | 4/2024 | Jang |
| 2024/0156355 A1 | 5/2024 | O'Brien et al. |
| 2024/0298907 A1 | 9/2024 | Bechtel et al. |
| 2024/0350019 A1 | 10/2024 | Pery-Shechter et al. |
| 2024/0364420 A1 | 10/2024 | Vallius et al. |
| 2025/0025058 A1 | 1/2025 | Bechtel et al. |
| 2025/0169696 A1 | 5/2025 | Dunn et al. |

FOREIGN PATENT DOCUMENTS

| | | |
|---|---|---|
| CN | 110301896 B | 10/2019 |
| CN | 211094079 U | 7/2020 |
| CN | 211131004 U | 7/2020 |
| CN | 112639582 A | 4/2021 |
| CN | 114466549 A | 5/2022 |
| EP | 3 002 568 A1 | 4/2016 |
| EP | 2 395 958 B1 | 12/2017 |
| EP | 3 384 841 A1 | 10/2018 |
| EP | 3 558 119 B1 | 11/2020 |
| EP | 3 886 686 | 10/2021 |
| EP | 3 903 676 A1 | 11/2021 |
| WO | WO 2024/052289 A1 | 3/2014 |
| WO | WO 2018/029123 A1 | 2/2018 |
| WO | WO 2019/149815 A1 | 8/2019 |
| WO | WO 2019/233903 A1 | 12/2019 |
| WO | WO 2020/030641 A1 | 2/2020 |

(56) References Cited

FOREIGN PATENT DOCUMENTS

| WO | WO 2020/114989 A1 | 6/2020 |
|---|---|---|
| WO | WO 2021/058338 A1 | 4/2021 |
| WO | WO 2021/094473 A1 | 5/2021 |
| WO | WO 2021/116766 A1 | 6/2021 |
| WO | WO 2021/116766 A8 | 6/2021 |
| WO | WO 2023/031927 A1 | 3/2023 |
| WO | WO 2023/245149 A2 | 12/2023 |
| WO | WO 2024/173585 A1 | 8/2024 |

OTHER PUBLICATIONS

U.S. Office Action from U.S. Appl. No. 18/991,054, dated Jun. 24, 2025, 23 pages.
Van Gastel, M. et al., "Camera-based pulse-oximetry—validated risks and opportunities from theoretical analysis", Biomedical Optics Express, Dec. 5, 2017, pp. 102-119, vol. 9, No. 1, Optical Society of America.
Website: "0.07mm Dia., TO-46 Package, InGaAs Photodiode", 2022, printed Dec. 7, 2022, 1 page, Edmund Optics Inc., https://www.edmundoptics.com/p/ingaas-detector-70mum-dia-to-46/12571/.
Website: "FlowMet Peripheral Blood Flow Monitoring System", updated Oct. 2022, printed Dec. 7, 2022, 7 pages, https://www.medtronic.com/us-en/healthcare-professionals/products/cardiovascular/intraprocedural-monitoring/flowmet.html.
Website: "Optical Solutions", Molex, dated 2023, printed May 10, 2023, 13 pages, Molex, LLC, https://www.molex.com/en-us/products/optical-solutions.
Website: "Track Your SpO2 to Uncover Changes in Your Wellbeing", Fitbit News, dated Sep. 7, 2020, printed Apr. 17, 2023, 7 pages, Fitbit, Inc., https://blog.fitbit.com/track-your-spo2/).626.
Wenz, J. J., "Examining water in model membranes by near infrared spectroscopy and multivariate analysis", BBA—Biomembranes, Dec. 9, 2017, pp. 673-682, Elsevier B.V., https://www.sciencedirect.com/science/article/pii/S0005273617303905.
Xu, J. et al., "Interferometric speckle visibility spectroscopy (ISVS) for human cerebral blood flow monitoring", APL Photonics, Dec. 4, 2020, pp. 126102-1 through 126102-10, vol. 5. AIP Publishing.
Xu, M. et al., "Laser Speckle Reduction Using a Motionless Despeckle Element Based on Random Mie Scattering", Journal of Display Technology, Nov. 12, 2013, pp. 151-156, vol. 10, No. 2, IEEE.
Yamakoshi, Y. et al., "Side-scattered finger-photoplethysmography: experimental investigations toward practical noninvasive measurement of blood glucose", Journal of Biomedical Optics, Jun. 2017, pp. 067001-1 through 067001-11, vol. 22, No. 6, SPIE.
Yao, Z. et al., "Integrated Silicon Photonic Microresonators: Emerging Technologies", IEEE Journal of Selected Topics in Quantum Electronics, Jun. 11, 2018, 24 pages, vol. 24, No. 6, IEEE.
Zalevsky, Z. et al., "Novel Approaches for Near and Far Field Super Resolved Imaging", 22nd Congress of the International Commision for Optics: Light for the Development of the World, Proc. of SPIE, Sep. 15, 2011, pp. 80116M-1 through 80116M-11, vol. 8011, No. 1, SPIE.
Zhang, J. et al., "III-V-on-Si photonic integrated circuits realized using micro-transfer-printing", APL Photonics, Nov. 4, 2019, pp. 110803-1 through 110803-10.
Zijlstra, W. G. et al., "Absorption Spectra of Human Fetal and Adult Oxyhemoglobin, De-Oxyhemoglobin, Carboxyhemoglobin, and Methemoglobin", Clinical Chemistry, Sep. 1991, pp. 1633-1638, vol. 37, No. 9, https://academic.oup.com/clinchem/article-abstract/37/9/1633/5649610?redirectedFrom=fulltext.
Zilkie, A. J. et al., "Multi-Micron Silicon Photonics Platform for Highly Manufacturable and Versitile Photonic Integrated Circuits", IEEE Journal of Selected Topics in Quantum Electronics, Apr. 15, 2019, 13 pages, vol. 25, No. 5, IEEE.
Zilkie, A. J. et al., "Power-efficient III-V/Silicon external cavity DBR lasers", Optics Express, Sep. 27, 2012, pp. 23456-23462, vol. 20, No. 21, Optical Society of America.
Akram, M. N. et al., "Laser speckle reduction due to spatial and angular diversity introduced by fast scanning micromirror", Applied Optics, Jun. 4, 2010, pp. 3297-3304, vol. 49, No. 17, Optical Society of America.
Abookasis, D. et al., Feasibility study of hidden flow imaging based on laser speckle technique using multiperspectives contrast images, Optics and Lasers in Engineering, 2014, pp. 38-45.
Apsel, S. et al., "Rolling-Shutter Laser Speckle Analysis in Bio-Photonics", Proc. of SPIE, Jun. 20, 2024, pp. 130060U-1-130060U-4, vol. 13006, SPIE.
Baek, H. J. et al., "The Effect of Optical Crosstalk on Accuracy of Reflectance-Type Pulse Oximeter for Mobile Healthcare", Journal of Healthcare Engineering, Oct. 21, 2018, 9 pages, vol. 2018, Article ID 3521738, Hindawi, https://doi.org/10.1155/2018/3521738.
Baets, R. et al., "Spectroscopy-on-chip applications of silicon photonics", Proc. Of SPIE, 2013, pp. 86270I-1 through 862701-10, vol. 8627, SPIE.
Berger, A. J. et al., "Feasibility of measuring blood glucose concentration by near-infrared Raman spectroscopy", Spectrochimica Acta Part A, 1997, pp. 287-292, Elsevier Science B.V.
Bi, R. et al., "A speckle-based method for fast blood flow measurement in deep tissue", Proceedings of SPIE, Optical Biopsy XIX: Toward Real-Time Spectroscopic Imaging and Diagnosis, Mar. 5, 2021, pp. 1163606-1 through 1163606-5, vol. 11636, SPIE.
Bi, R. et al., "Fast pulsatile blood flow measurement in deep tissue through a multimode detection fiber", Journal of Biomedical Optics, May 13, 2020, pp. 055003-1 through 055003-10, vol. 25(5), SPIE.
Biswas, A. et al., "Fast diffuse correlation spectroscopy with a low-cost, fiber-less embedded diode laser", Biomedical Optics Express, Oct. 4, 2021, pp. 6686-6700, vol. 12, No. 11, Optical Society of America.
Brouckaert, J. et al., "Silicon-on-Insulator Microspectrometer", Proceedings Symposium IEEE/LEOS Benelux Chapter, 2008, pp. 7-10, IEEE.
Cole, D. B. et al., "Integrated heterodyne interferometer with on-chip modulators and detectors", Optics Letters, Jun. 25, 2015, pp. 3097-3100, vol. 40, No. 13, Optical Society of America.
Epping, J. P. et al., "High power, tunable, narrow linewidth dual gain hybrid laser", Laser Congress, Oct. 3, 2019, pp. 1-2.
European Patent Office Communication pursuant to Rule 114(2) EPC, for Patent Application No. 22776935.3, mailed Aug. 9, 2024, 6 pages.
Fu, D. et al., "In Vivo Metabolic Fingerprinting of Neutral Lipids with Hyperspectral Stimulated Raman Scattering Microscopy", Journal of the American Chemical Society, May 28, 2014, pp. 8820-8828, American Chemical Society Publications.
Fukui, T. et al., "Single-Pixel Imaging Using Multimode Fiber and Silicon Photonic Phased Array", Journal of Lightwave Technology, Jul. 14, 2020, pp. 839-844, vol. 39, No. 3, IEEE.
Ge, Z. et al., "Dynamic laser speckle analysis using the event sensor", Applied Optics, Dec. 23, 2020, pp. 172-178, vol. 60, No. 1, Optical Society of America.
Ghijsen, M. et al., "Wearable speckle plethysmography (SPG) for characterizing microvascular flow and resistance", Biomedical Optics Express, Jul. 30, 2018, pp. 3937-3952, vol. 9, No. 8, Optical Society of America under the terms of the OSA Open Access Publishing Agreement.
Goodman, J. W., "Some fundamental properties of speckle", Journal of the Optical Society of America, Nov. 1976, pp. 1145-1150, vol. 66, No. 11, Optical Society of America.
Gottschling, K. et al., "Molecular Insights into Carbon Dioxide Sorption in Hydrazone-Based Covalent Organic Frameworks with Tertiary Amine Moieties", Chemistry of Materials, Feb. 13, 2019, pp. 1946-1955, American Chemical Society.
Hashimoto, Y. et al., "Fabrication of an Anti-Reflective and Super-Hydrophobic Structure by Vacuum Ultraviolet Light-Assisted Bonding and Nanoscale Pattern Transfer", Micromachines, Apr. 15, 2018, pp. 1-11, www.mdpi.com/journal/micromachines.
Hollis, V. S. et al., "Non-invasive monitoring of brain tissue temperature by near-infrared spectroscopy", Proceedings of SPIE, Optical Tomography and Spectroscopy of Tissue IV, Jun. 29, 2001, pp. 470-481, vol. 4250, SPIE, https://www.spiedigitallibrary.org/

(56) References Cited

OTHER PUBLICATIONS conference-proceedings-of-spie/4250/1/Noninvasive-monitoring-of-brain-tissue-temperature-by-near-infrared-spectroscopy/10.1117/12.434506.short?SSO=1.
International Search Report and Written Opinion of the International Searching Authority, Mailed Mar. 11, 2021, Corresponding to PCT/IB2020/001037, 13 pages.
International Search Report and Written Opinion of the International Searching Authority, mailed Apr. 4, 2023, corresponding to PCT/EP2022/082341, 33 pages.
International Search Report and Written Opinion of the International Searching Authority, mailed Feb. 1, 2022, corresponding to PCT/IB2021/000649, 18 pages.
International Search Report and Written Opinion of the International Searching Authority, mailed Nov. 15, 2021, corresponding to PCT/IB2021/000517, 15 pages.
International Search Report and Written Opinion of the International Searching Authority, mailed Oct. 10, 2022, corresponding to PCT/IB2022/000373, 16 pages.
International Search Report and Written Opinion of the International Searching Authority, mailed Oct. 19, 2022, corresponding to PCT/EP2022/071467, 16 pages.
International Search Report and Written Opinion of the International Searching Authority, mailed Feb. 14, 2023, corresponding to PCT/EP2022/082162, 33 pages.
International Search Report and Written Opinion of the International Searching Authority, Mailed Dec. 11, 2024, Corresponding to PCT/IB2024/000388, 14 pages.
International Search Report and Written Opinion of the International Searching Authority, mailed May 14, 2025, corresponding to PCT/IB2025/000071, 15 pages.
International Search Report and Written Opinion of the International Searching Authority, mailed Jan. 2, 2023, corresponding to PCT/EP2022/074876, 13 pages.
Invitation to Pay Additional Fees and Partial Search Report mailed Feb. 14, 2023 in related International Application No. PCT/EP2022/082341, 18 pages.
Izutsu, M. et al., "Integrated Optical SSB Modulator/Frequency Shifter", IEEE Journal of Quantum Electronics, Nov. 1981, pp. 2225-2227, vol. QE-17, No. 11, IEEE.
Kang, J. W. et al., "Direct observation of glucose fingerprint using in vivo Raman spectroscopy," Science Advances, Jan. 24, 2020, pp. 1-8, American Association for the Advancement of Science.
Karlsson, C. J. et al., "All-fiber multifunction continuous-wave coherent laser radar at 1.55 µm for range, speed, vibration, and wind measurements", Applied Optics, Jul. 20, 2000, pp. 3716-3726, vol. 39, No. 21, Optical Society of America.
Lai, M. et al., "Perfusion Monitoring By Contactless Photoplethysmography Imaging", 2019 IEEE 16th International Symposium on Biomedical Imaging (ISBI 2019), Venice, Italy, Apr. 8-11, 2019, pp. 1778-1782, IEEE.
Lai, N. et al., "CO2 Capture With Absorbents of Tertiary Amine Functionalized Nano-SiO2", Frontiers in Chemistry, Feb. 28, 2020, pp. 1-9, vol. 8, Article 146, www.frontiersin.org.
Lapchuk, A. et al., "Investigation of speckle suppression beyond human eye sensitivity by using a passive multimode fiber and a multimode fiber bundle", Applied Optics, Feb. 21, 2020, pp. 6820-6834, vol. 28, No. 5, Optical Society of America.
Liu, X. et al., "Simultaneous measurements of tissue blood flow and oxygenation using a wearable fiber-free optical sensor", Journal of Biomedical Optics, Jan. 29, 2021, pp. 012705-1 through 012705-15, vol. 26, No. 1, SPIE.
Loi, R. et al., "Transfer Printing of AlGaInAs/InP Etched Facet Lasers to Si Substrates", IEEE Photonics Journal, Nov. 11, 2016, 11 pages, vol. 8, No. 6, IEEE.
Lu, H. et al., "Single-trial estimation of the cerebral metabolic rate of oxygen with imaging photoplethysmography and laser speckle contrast imaging", Optics Letters, Mar. 17, 2015, pp. 1193-1196, vol. 40, No. 7, Optical Society of America.
Mehta, D. S. et al., "Laser speckle reduction by multimode optical fiber bundle with combined temporal, spatial, and angular diversity", Applied Optics, Apr. 11, 2012, pp. 1894-1904, vol. 51, No. 12, Optical Society of America.
Merritt, S. et al., "Monitoring temperature non-invasively using broadband Diffuse Optical Spectroscopy", OSA/FIO, 2004, 1 page, Optical Society of America, https://opg.optica.org/abstract.cfm?URI=FiO-2004-FTuK4.
Mosso, E. et al., "Cluster speckle structures through multiple apertures forming a closed curve", Optics Communications, 2010, pp. 1285-1290, Elsevier B.V.
Nabeel, P. M. et al., "Local Pulse Wave Velocity: Theory, Methods, Advancements, and Clinical Applications", IEEE Reviews in Biomedical Engineering, Jul. 29, 2019, pp. 74-112, vol. 13, IEEE.
Noriki, A. et al., "45-degree curved micro-mirror for vertical optical I/O of silicon photonics chip", Optics Express, Jul. 1, 2019, pp. 19749-19757, vol. 27, No. 14, Optical Society of America, https://doi.org/10.1364/OE.27.019749.
Poulton, C. V. et al., "Frequency-modulated Continuous-wave LIDAR Module in Silicon Photonics", OFC, 2015, 4 pages, Optical Society of America.
Qiu, J. et al., "Correcting speckle contrast at small speckle size to enhance signal to noise ratio for laser speckle contrast imaging", Optics Express, Nov. 15, 2013, pp. 28902-28913, vol. 21, No. 23, Optical Society of America.
Redding, B. et al., "Compact spectrometer based on a disordered photonic chip", Nature Photonics, Jul. 28, 2013, pp. 746-751, vol. 7, Macmillan Publishers Limited.
Redding, B. et al., "Evanescently coupled multimode spiral spectrometer", Optica, Aug. 25, 2016, pp. 956-962, vol. 3, No. 9, Optical Society of America.
Robinson, M. B., "Interferometric diffuse correlation spectroscopy improves measurements at long source-detector separation and low photon count rate", Journal of Biomedical Optics, Sep. 30, 2020, pp. 097004-1 through 097004-12, vol. 25, No. 9, SPIE.
Roelkens, G. et al., "Transfer printing for silicon photonics transceivers and interposers", 2018 IEEE Optical Interconnects Conference, Jun. 4, 2018, pp. 13-14, IEEE.
Ryckeboer, E., "Spectroscopic Detection of Glucose with a Silicon Photonic Integrated Circuit", Universiteit Gent, Jan. 1, 2014, 263 pages, ISBN 978-90-8578-688-7, http://www.photonics.intec.ugent.be/download/phd_206.pdf.
Schneider, S. et al., "Optical coherence tomography system mass-producible on a silicon photonic chip", Optics Express, Jan. 20, 2016, pp. 1573-1586, vol. 24, No. 2, Optical Society of America.
Sdobnov, A. Y. et al. "Speckle dynamics under ergodicity breaking", Journal of Physics D: Applied Physics, Mar. 26, 2018, pp. 1-21, vol. 51, No. 15, IOP Publishing Ltd.
Shimotsu, S. et al., "Single Side-Band Modulation Performance of a LiNbO3 Integrated Modulator Consisting of Four-Phase Modulator Waveguides", IEEE Photonics Technology Letters, Apr. 2001, pp. 364-366, vol. 13, No. 4, IEEE.
Subramanian, A. Z. et al., "Silicon and silicon nitride photonic circuits for spectroscopic sensing on-a-chip [Invited]", Photon. Res., Aug. 28, 2015, pp. B47-B59, vol. 3, No. 5, Chinese Laser Press.
Teng, Zhongshuai et al., "In Vivo Pulse Wave Measurement Through a Multimode Fiber Diffuse Speckle Analysis System", Frontiers in Physics, Jan. 19, 2021, pp. 1-8, vol. 8, Article 613342, www.frontiersin.org.
Timm, U. et al., "Non-Invasive Optical Real-time Measurement of Total Hemoglobin Content", Procedia Engineering, 2010, pp. 488-491, Elsevier Ltd.
Tran, T-T-K. et al., "Speckle reduction in laser projection displays through angle and wavelength diversity", Applied Optics, Feb. 16, 2016, pp. 1267-1274, vol. 55, No. 6, Optical Society of America.
Tuchin, V., "Chapter 8: Coherent Effects at the Interaction of Laser Radiation with Tissues and Cell Flows", Tissue Optics Light Scattering Methods and Instruments for Medical Diagnostics, 3rd Edition, 2015, pp. 359-417, SPIE.
U.S. Advisory Action for U.S. Appl. No. 17/822,419, dated May 2, 2024, 5 pages.

(56) References Cited

OTHER PUBLICATIONS

U.S. Advisory Action for U.S. Appl. No. 17/822,419, dated Oct. 10, 2023, 6 pages.
U.S. Appl. No. 18/991,054, filed Dec. 20, 2024.
U.S. Notice of Allowance for U.S. Appl. No. 17/703,920, dated Jul. 31, 2024, 10 pages.
U.S. Notice of Allowance from U.S. Appl. No. 17/757,130, dated Jan. 18, 2023, 10 pages.
U.S. Notice of Allowance from U.S. Appl. No. 17/822,419, dated Nov. 6, 2024, 10 pages.
U.S. Office Action for U.S. Appl. No. 17/703,920, dated Apr. 5, 2024, 11 pages.
U.S. Office Action for U.S. Appl. No. 17/822,419, dated Feb. 20, 2024, 12 pages.
U.S. Office Action for U.S. Appl. No. 17/822,419, dated Jun. 12, 2024, 12 pages.
U.S. Office Action for U.S. Appl. No. 17/822,419, dated Nov. 3, 2023, 18 pages.
U.S. Office Action from U.S. Appl. No. 17/711,974, dated Oct. 11, 2024, 18 pages.
U.S. Office Action from U.S. Appl. No. 17/822,419, dated Jul. 20, 2023, 21 pages.
U.S. Office Action from U.S. Appl. No. 17/822,419, dated Mar. 10, 2023, 17 pages.
U.S. Office Action from U.S. Appl. No. 17/934,502, dated Aug. 31, 2023, 6 pages.
U.S. Office Action from U.S. Appl. No. 17/934,502, dated Feb. 1, 2024, 6 pages.
U.S. Office Action from U.S. Appl. No. 17/934,502, dated Jun. 5, 2024, 7 pages.
U.S. Office Action from U.S. Appl. No. 18/778,893, dated Apr. 22, 2025, 9 pages.
U.S. Office Action from U.S. Appl. No. 18/991,054, dated Mar. 3, 2025, 19 pages.
Valley, G.C. et al., "Multimode waveguide speckle patterns for compressive sensing", Optics Letters, May 23, 2016, pp. 2529-2532, vol. 41, No. 11, Optical Society of America.
International Search Report and Written Opinion of the International Searching Authority, mailed Jun. 23, 2025, corresponding to PCT/IB2025/000070, 15 pages.

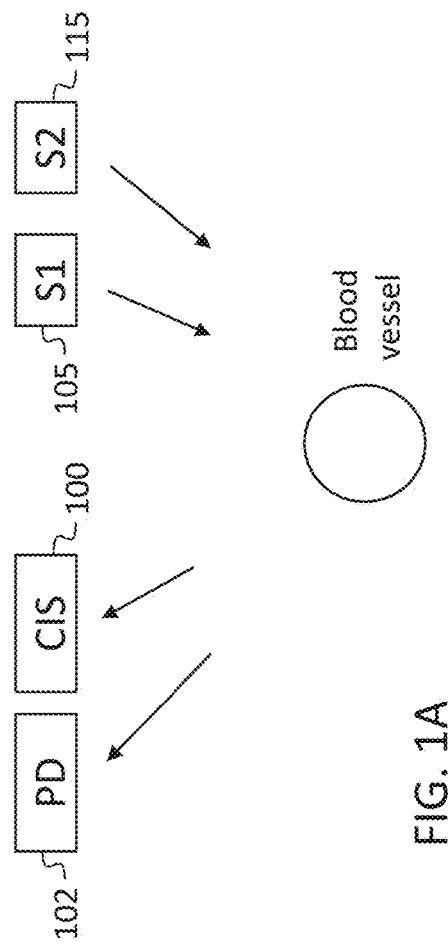
FIG. 1A
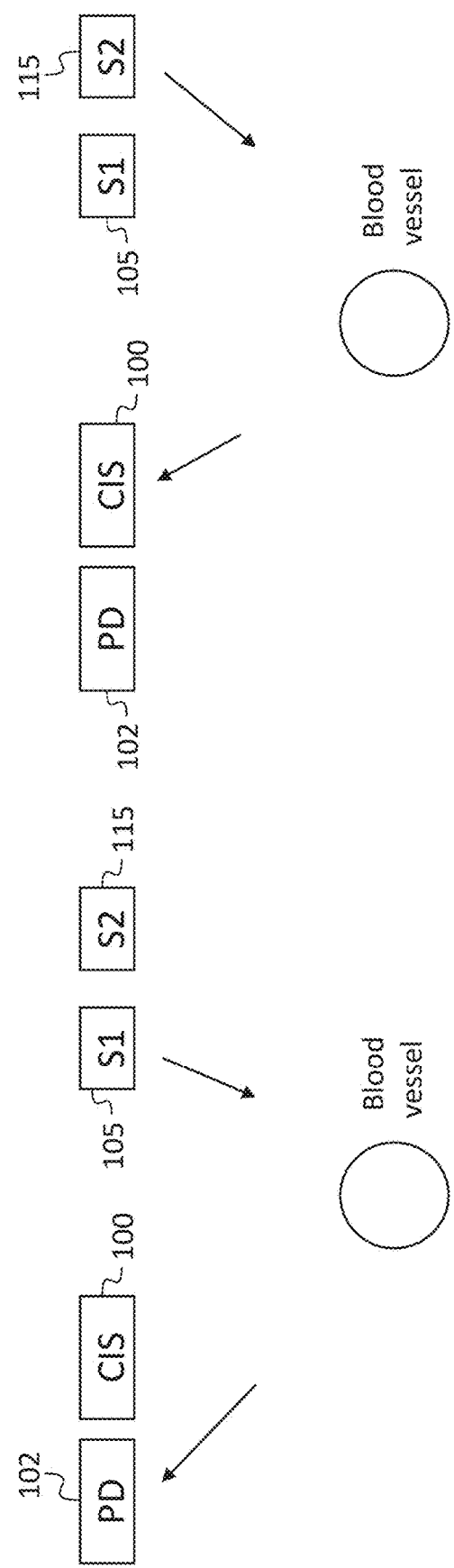
FIG. 1B
FIG. 1C

WEARABLE DEVICE WITH LIGHT SOURCE AND OPTICAL SENSOR

CROSS-REFERENCE TO RELATED APPLICATION(S)

The present application claims priority to and the benefit of U.S. Provisional Application No. 63/726,157, filed Nov. 27, 2024, entitled "WEARABLE DEVICE WITH LIGHT SOURCE AND OPTICAL SENSOR", the entire content of which is incorporated herein by reference.

FIELD

One or more aspects of embodiments according to the present disclosure relate to biomarker monitoring, and more particularly to a system and method for measuring one or more biomarkers using one or more light sources and one or more optical sensors.

BACKGROUND

Various cardiovascular biomarkers may be clinically significant, including, for example, the blood pressure of a subject.

It is with respect to this general technical environment that aspects of the present disclosure are related.

SUMMARY

According to an embodiment of the present disclosure, there is provided a system, including: a wearable device for being worn by a subject and for measuring a first biomarker of a blood vessel of the subject, the wearable device including: a first light source, and a plurality of optical detectors, the system being configured: to perform a photoplethysmography measurement with each of the plurality of optical detectors, the first biomarker being a blood volume; or to perform a speckleplethysmography measurement with each of the plurality of optical detectors, the first biomarker being a blood flow velocity.

In some embodiments, the system is configured to read interleaved data from the plurality of optical detectors.

In some embodiments, the system is further configured: to read first interleaved data from a first subset of the plurality of optical detectors; and to read second interleaved data from a second subset of the plurality of optical detectors.

In some embodiments, the system is configured: to perform a first measurement, with a first optical detector of the plurality of optical detectors; to perform a second measurement, with a second optical detector of the plurality of optical detectors, the second optical detector being azimuthally separated from the first optical detector; and to determine that a measure of signal quality of the first measurement exceeds a measure of signal quality of the second measurement.

In some embodiments, the system is further configured: in response to the determining that the measure of signal quality of the first measurement exceeds the measure of signal quality of the second measurement, to perform a third measurement, with the first optical detector.

In some embodiments, the system is further configured: to read first interleaved data from a first subset of the plurality of optical detectors; and to read second interleaved data from a second subset of the plurality of optical detectors, wherein the first optical detector is an optical detector of the first subset, and the second optical detector is an optical detector of the second subset.

In some embodiments, the system is further configured: in response to the determining that the measure of signal quality of the first measurement exceeds the measure of signal quality of the second measurement, to prompt a user of the system to perform an azimuthal adjustment of the wearable device.

In some embodiments: the first biomarker is a blood flow velocity, and the plurality of optical detectors includes a first image sensor and a second image sensor azimuthally separated from the first image sensor.

In some embodiments, the first image sensor is a zero chief ray angle image sensor.

In some embodiments, an optical path between the blood vessel of the subject and the first image sensor includes no lenses.

In some embodiments, the wearable device further includes a receiving window, and the length of an optical path between the receiving window and an optical detector of the plurality of optical detectors is less than 15 mm.

In some embodiments, the wearable device further includes a receiving window, and a distance between the receiving window and an optical detector of the plurality of optical detectors is less than 5 mm.

In some embodiments: the wearable device further includes a second light source; and the system is further configured: to perform a photoplethysmography measurement with the second light source and an optical detector of the plurality of optical detectors; or to perform a speckleplethysmography measurement with the second light source and an optical detector of the plurality of optical detectors.

According to an embodiment of the present disclosure, there is provided a system, including: a wearable device for being worn by a subject and for measuring a first biomarker of a blood vessel of the subject, the wearable device including: a plurality of light sources, and a first optical detector, the system being configured: to perform a photoplethysmography measurement with each of the plurality of light sources, the first biomarker being a blood volume; or to perform a speckleplethysmography measurement with each of the plurality of light sources, the first biomarker being a blood flow velocity.

In some embodiments, the system is configured: to perform a first measurement, with a first light source of the plurality of light sources; to perform a second measurement, with a second light source of the plurality of light sources, the second light source being azimuthally separated from the first light source; and to determine that a measure of signal quality of the first measurement exceeds a measure of signal quality of the second measurement.

In some embodiments, the system is further configured: in response to the determining that the measure of signal quality of the first measurement exceeds the measure of signal quality of the second measurement, to perform a third measurement, with the first light source.

In some embodiments, the system is further configured: in response to the determining that the measure of signal quality of the first measurement exceeds the measure of signal quality of the second measurement, to prompt a user of the system to perform an azimuthal adjustment of the wearable device.

In some embodiments: the wearable device further includes a second optical detector; and the system is further configured: to perform a photoplethysmography measurement with a light source of the plurality of light sources and the second optical detector; or to perform a speckleplethysmography measurement with a light source of the plurality of light sources and the second optical detector.

BRIEF DESCRIPTION OF THE DRAWINGS

These and other features and advantages of the present disclosure will be appreciated and understood with reference to the specification, claims, and appended drawings wherein:

FIG. 1A is a schematic drawing of a health sensor, according to an embodiment of the present disclosure;

FIG. 1B is a schematic drawing of a health sensor, according to an embodiment of the present disclosure;

FIG. 1C is a schematic drawing of a health sensor, according to an embodiment of the present disclosure;

DETAILED DESCRIPTION

Figure 1D:
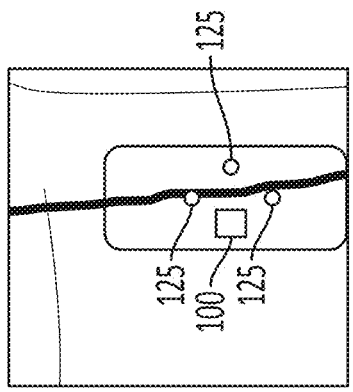
FIG. 1D is a schematic drawing of a health sensor, according to an embodiment of the present disclosure.

The detailed description set forth below in connection with the appended drawings is intended as a description of exemplary embodiments of a wearable device with a light source and an optical sensor provided in accordance with the present disclosure and is not intended to represent the only forms in which the present disclosure may be constructed or utilized. The description sets forth the features of the present disclosure in connection with the illustrated embodiments. It is to be understood, however, that the same or equivalent functions and structures may be accomplished by different embodiments that are also intended to be encompassed within the scope of the disclosure. As denoted elsewhere herein, like element numbers are intended to indicate like elements or features.

Referring to FIG. 1A, a health sensor (e.g., a cuffless blood pressure sensor) may include one or more light sources 110 for illuminating one or more blood vessels in a patient, or "subject", and optical detectors 120 (e.g., a photodiode (PD) 102 or an image sensor 100 (e.g., a CMOS image sensor (CIS)) for receiving light scattered from the blood vessel (e.g., from blood inside the blood vessel). The health sensor may include (i) a photoplethysmography (PPG) sensor including a source of incoherent light 105 (e.g., S1, in FIG. 1A) and a photodetector (e.g., a single-pixel photodetector such as a photodiode 102 (PD)) for measuring the instantaneous blood volume in the blood vessel, and (ii) a speckleplethysmography (SPG) sensor (including a source of coherent light such as a laser 115 (e.g., S2, in FIG. 1A) and an image sensor 100 (e.g., a CMOS image sensor (CIS) or a charge-coupled device (CCD)) for measuring the instantaneous blood velocity in the blood vessel. Each of the instantaneous blood volume in the blood vessel, and the instantaneous blood velocity may vary with the cardiac cycle; blood pressure (both the systolic blood pressure and the diastolic blood pressure) may be inferred from a time history (or "time series") of instantaneous blood volume measurements and a time history of instantaneous blood velocity measurements.

FIG. 1B shows the performing of a photoplethysmography measurement (with the blood vessel illuminated by the source of incoherent light, and the photodiode 102 (PD)) being used to detect the light scattering from the blood vessel into the photodiode 102. FIG. 1C shows the performing of a speckleplethysmography measurement (with the blood vessel illuminated by the source of coherent light S2, and the image sensor 100 (labeled CIS) being used to detect the light scattering from the blood vessel into the image sensor 100. When a speckleplethysmography measurement is performed, the measured speckle contrast (which is a measurement that is time-averaged over the exposure time of the image sensor 100) may decrease with increasing blood flow velocity (which may cause the speckle pattern on the image sensor 100 to change more rapidly); as such, the measured speckle contrast may be used as an indication of blood flow velocity.

Each image (or frame) generated by the image sensor 100 may be processed to calculate a data point of a time series representing a biomarker. One such biomarker may be, as mentioned above, a value that is representative of flow of blood in an artery. In such a case the alignment of the light source 110 and image sensor 100 may be such that the light scattered by the flowing blood in the artery is able to be captured by the imaging device.

For the case in which a health sensor based on laser speckle imaging (e.g., a health sensor based on speckleplethysmography) is used in a wearable device to measure the blood flow in a particular anatomical feature such as an artery, for example the radial artery at the wrist, a need to align the sensor with this anatomical feature may make the sensor performance highly dependent on device placement. The small radial artery diameter (2-3 mm) combined with the limited sensing volume offered by a sensor consisting of a single light source 110 and single image sensor 100 may contribute to this dependency on device placement.

Placing a wearable device over a non-visible blood vessel such as the radial artery on the volar side of the wrist may be challenging, especially when the body of the wearable device itself obstructs the view of skin when placed in the general area of the artery. This limits the user's ability to align the emission and detection windows of the wearable device with a location on the skin that might have been identified pre-placement via ultrasound imaging or palpitation. This last issue may be mitigated somewhat using datums on the body of the wearable device that may be positioned relative to landmarks of the subject's anatomy for alignment to the wearable device's optimal sensing point. A multi-step placement process involving first locating the blood vessel (e.g., by palpitation) relative to landmarks of the subject and then placing the wearable device at a location defined by the landmarks may be challenging for an untrained user, however. As used herein, the subject is a person wearing the wearable device, and the "user" is a person operating the wearable device. The user may be the subject or another person, e.g., a clinician.

Figure 1E:
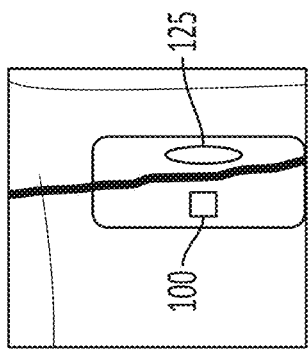
FIG. 1E is a schematic drawing of a health sensor, according to an embodiment of the present disclosure.
Figure 1F:
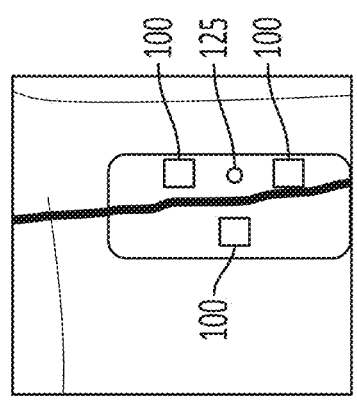
FIG. 1F is a schematic drawing of a health sensor, according to an embodiment of the present disclosure.
Figure 1I:
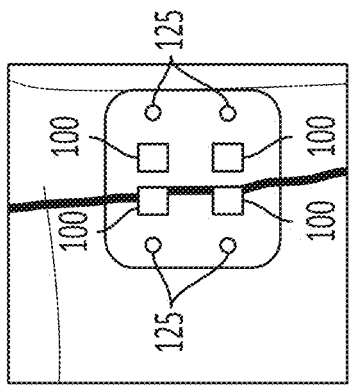
FIG. 1I is a schematic drawing of a health sensor, according to an embodiment of the present disclosure.
Figure 1H:
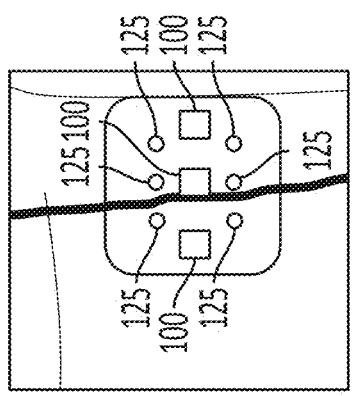
FIG. 1H is a schematic drawing of a health sensor, according to an embodiment of the present disclosure.
Figure 1K:
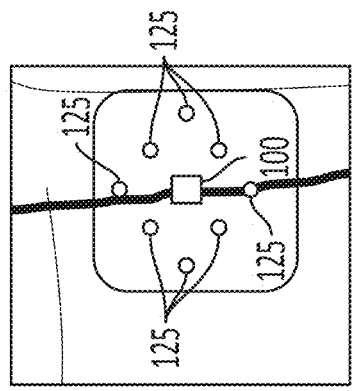
FIG. 1K is a schematic drawing of a health sensor, according to an embodiment of the present disclosure.
Figure 1G:
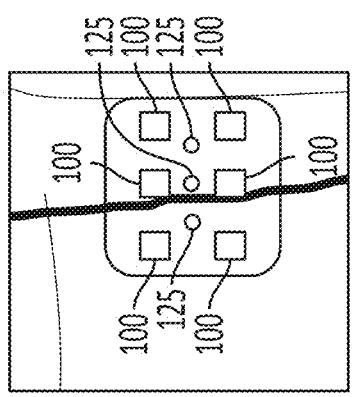
FIG. 1G is a schematic drawing of a health sensor, according to an embodiment of the present disclosure.
Figure 1J:
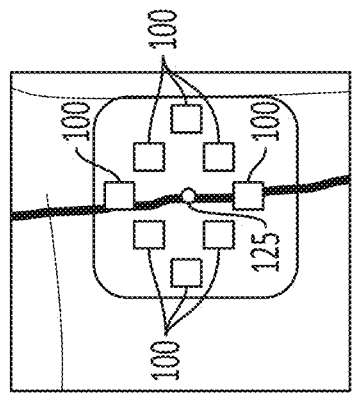
FIG. 1J is a schematic drawing of a health sensor, according to an embodiment of the present disclosure.

Various aspects of the design of the wearable device may affect sensitivity to alignment. FIG. 1D shows an illumination shape in which the laser beam 125 is highly elliptical, so as to illuminate more tissue while not greatly impacting source-detector separation. Such a configuration may impact signal-to-noise ratio (SNR) performance by the addition of light not travelling through the radial artery, however. FIG. 1E shows a configuration with multiple emitters (e.g., multiple lasers 115) illuminating, with multiple respective laser beams 125, the tissue of the subject, and the artery. In such an embodiment, the lasers 115 may be turned on one at a time, to identify the laser 115 associated with the best signal-to-noise ratio performance. FIG. 1F shows an embodiment with multiple optical detectors 120. For example, three image sensors 100 may be operated in "multi-sensor" mode where frames are captured sequentially from each sensor. The effective frame rate may be divided by 3 (in the case of using 3 image sensors 100). In some such embodiments, the image sensor 100 with the best performance (which may depend on the location, relative to the light source 110 and the artery, of each of the image sensors 100) may be identified and the wearable device may then transition to using only this image sensor 100, at full frame rate. FIGS. 1G-1I show embodiments with multiple light sources 110 (e.g., multiple lasers 115 illuminating the tissue of the subject with multiple respective laser beams 125) and multiple optical detectors 120. FIGS. 1J and 1K show, respectively, an embodiment with multiple optical detectors 120 and one light source 110, and with multiple light sources 110 and one optical detector 120.

As mentioned above, to reduce the positional sensitivity of a sensor the number of transmitting elements or the number of receiving elements may be increased. In the case of a laser-based speckle imaging sensor (e.g., in the case of a speckleplethysmography sensor) this may be accomplished by increasing the number of lasers 115 or the number of image sensors 100 (or both). If multiple lasers 115 (that are not phase coherent with each other) are used, then only one laser 115 may be turned on at a time, to avoid the reduction in speckle contrast that may otherwise occur when light from several lasers 115 is received at an image sensor 100. For a convex, generally cylindrical part of the subject (such as a finger, a limb, the neck, or the torso of the subject) (which may be referred to as a "convexity" of the subject) with a blood vessel (e.g., the radial artery) extending generally parallel to, and offset from a central axis of, the part (as, for example, the radial artery at the wrist extends generally parallel to the arm and near the skin) the degree of freedom in which accurate placement may be important may be the "azimuthal" position of the sensor (which for a band securing the wearable device to the wrist may be adjusted by rotating the band (along with the wearable device) around the wrist (about the longitudinal axis of the forearm)).

Figure 2A:
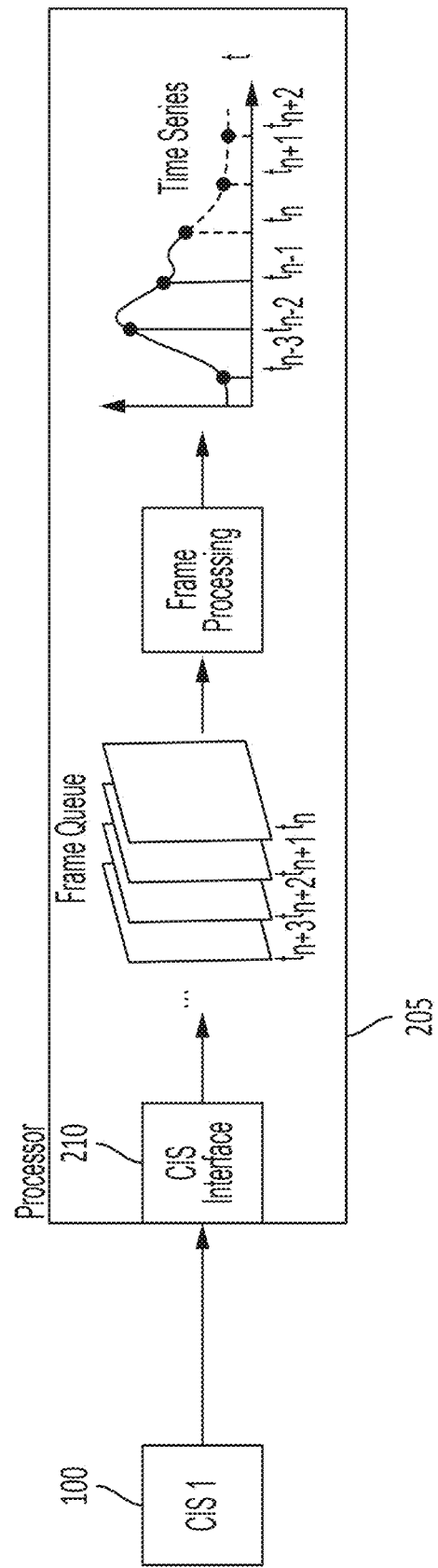
FIG. 2A is a schematic drawing of an images sensor and processor interface, according to an embodiment of the present disclosure.

Using multiple image sensors 100 offers the capability to detect over a broader physical space and cover regions where the scattered light would be generally lost when a single sensor is employed. FIG. 2A shows a simplified signal chain of the receiving elements of the wearable device. An image sensor 100 transmits image data (frames) to a processor 205 (e.g., a processing circuit) (such as a microcontroller (MCU) or field programmable gate array (FPGA)). The processor 205 receives frame data from the image sensor 100 via an interface 210 (such as a parallel bus interface or a serial interface such as the Camera Serial Interface (CSI) (promulgated by the Mobile Industry Processor Interface (MIPI) Alliance). The frames may be queued before frame processing. The queue may have a length of zero in which case frame processing occurs immediately. Frame processing extracts information from each frame received, resulting in value representative of the state of the speckle in the imaged frame captured at a time t. This value may be, for example, a measured speckle contrast. The image sensor 100 operates at a frame rate which may define the sample rate of the time series.

Figure 2B:
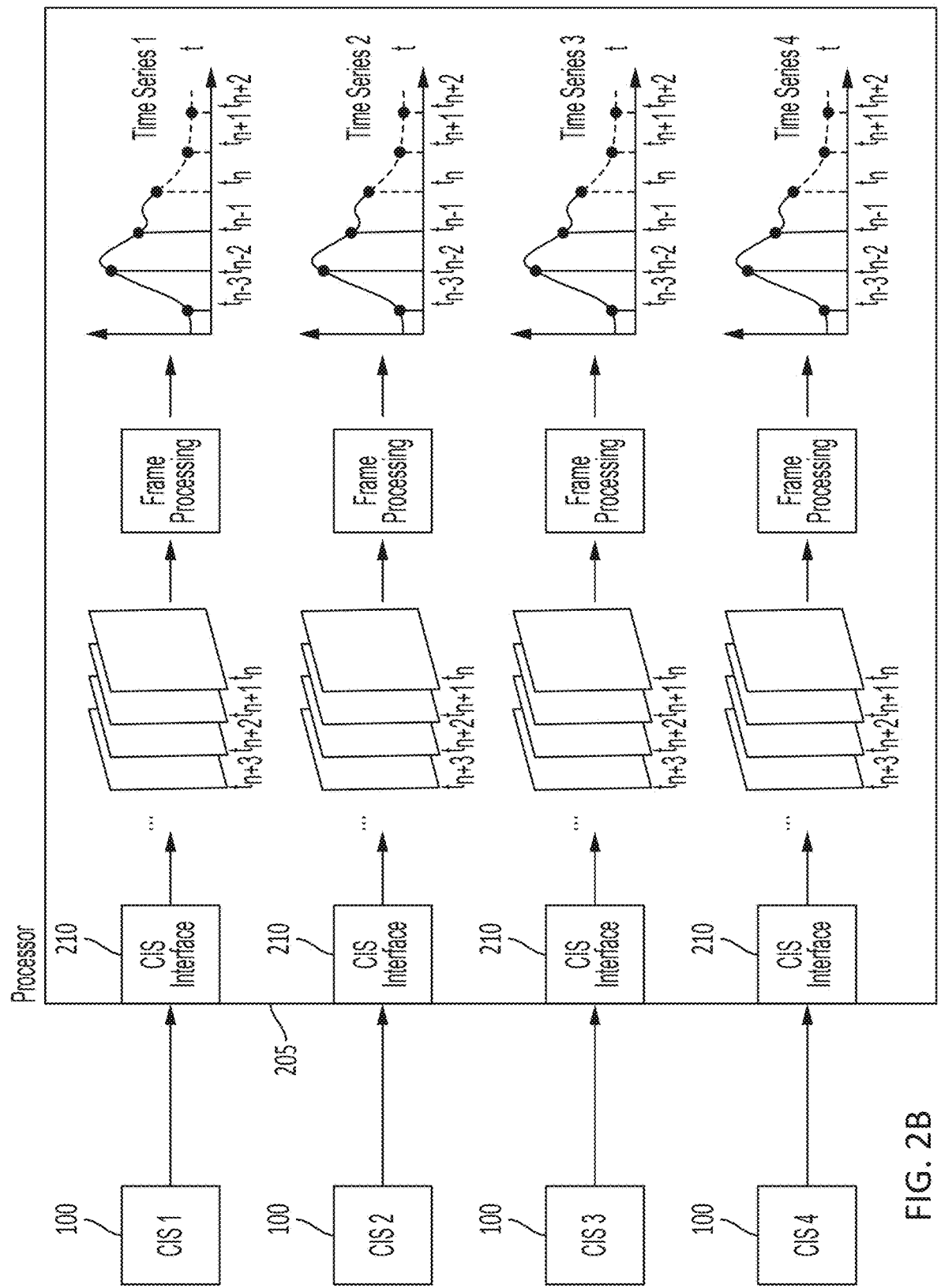
FIG. 2B is a schematic drawing of a plurality of images sensors and processor interfaces, according to an embodiment of the present disclosure.

In some embodiments, multiple image sensors 100 are operated in parallel as illustrated in FIG. 2B. In the example shown, four image sensors 100 are shown but the design may be employed with more or fewer image sensors 100. The processor 205 in this embodiment need not be a single processor 205 but may be a distributed processor 205, including a plurality of processors 205.

Figure 2C:
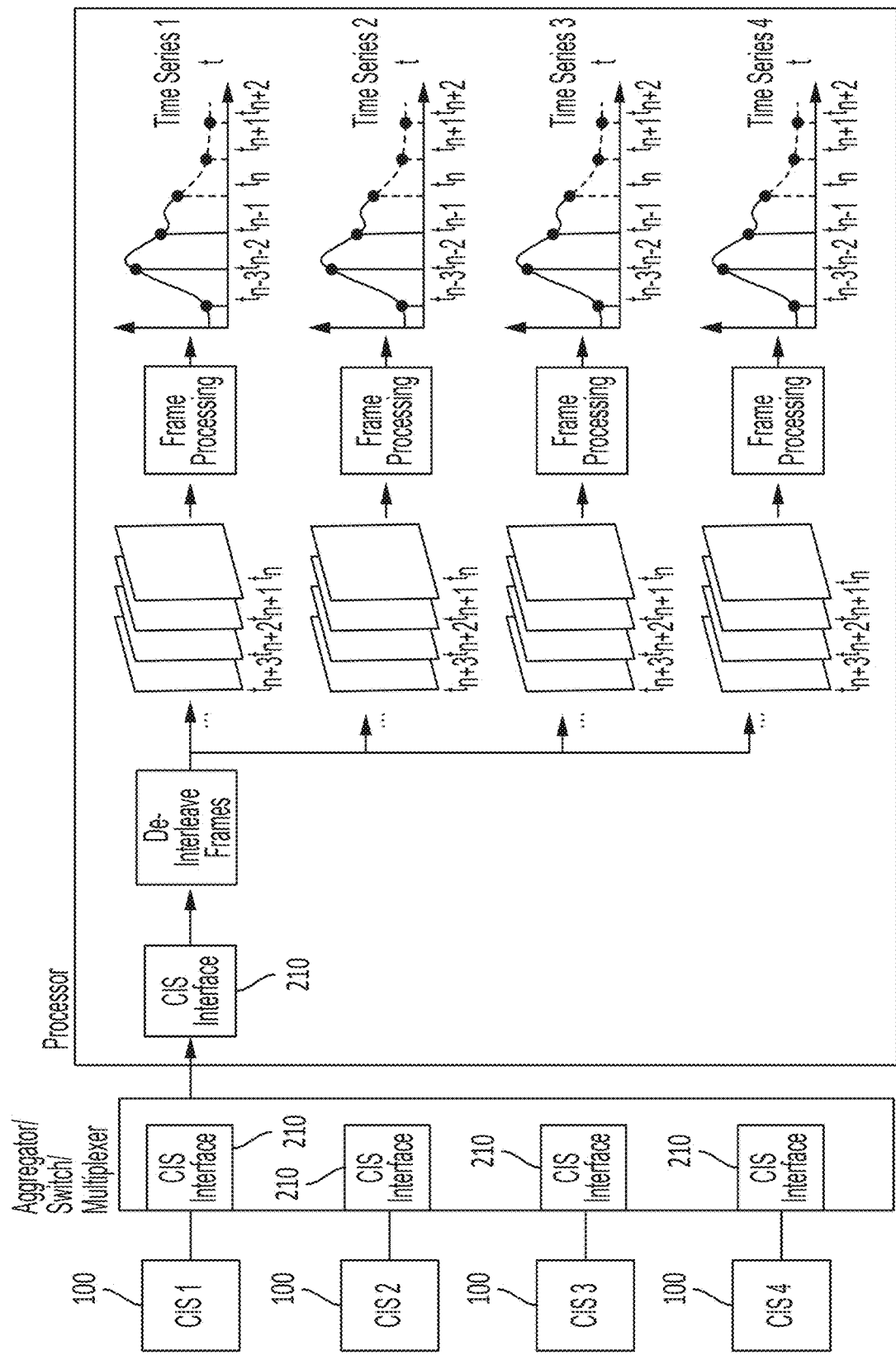
FIG. 2C is a schematic drawing of a plurality of images sensors and processor interfaces, according to an embodiment of the present disclosure.

In some embodiments, multiple image sensors 100 share a communication bus and an interface 210 with the processor 205, as shown in FIG. 2C. The processor 205 may have a limited number of sensor interfaces 210. An aggregator or switch or multiplexer (external to the processor 205) may be connected to the image sensors 100, and, in operation, may interleave their frame streams and transmit the resulting composite stream to the processor 205 through a single CIS interface 210. In some embodiments, a switch or multiplexer is employed to switch between generated frames, so the processor 205 receives an interleaved sequence. A switch may also be employed in a non-interleaved or non-simultaneous sampling embodiment. In such an embodiment, each image sensor 100 may be monitored for a few seconds sequentially to assess signal quality. The optimal image sensor 100 may then be identified. In this embodiment the image sensors 100 may capture frames at a simultaneous point in time at a frame rate F and transmit those frames to the processor 205 at rate NF (where N is the number of image sensors 100; e.g., N=4 in the embodiment of FIG. 2C). In some embodiments, the image sensors 100 instead capture frames sequentially, so that the rate at which each sensor runs is F/N, and the rate at which the frames are sent to the processor 205 is equal to F. In both cases the captured frames may be de-interleaved, e.g., in the processor 205 (or in a separate de-interleaving circuit) to separate into N respective streams the frames from the N image sensors 100. The processor 205 may then process the frames provided by the image sensors 100 in parallel, as illustrated in FIG. 2C.

Figure 2D:
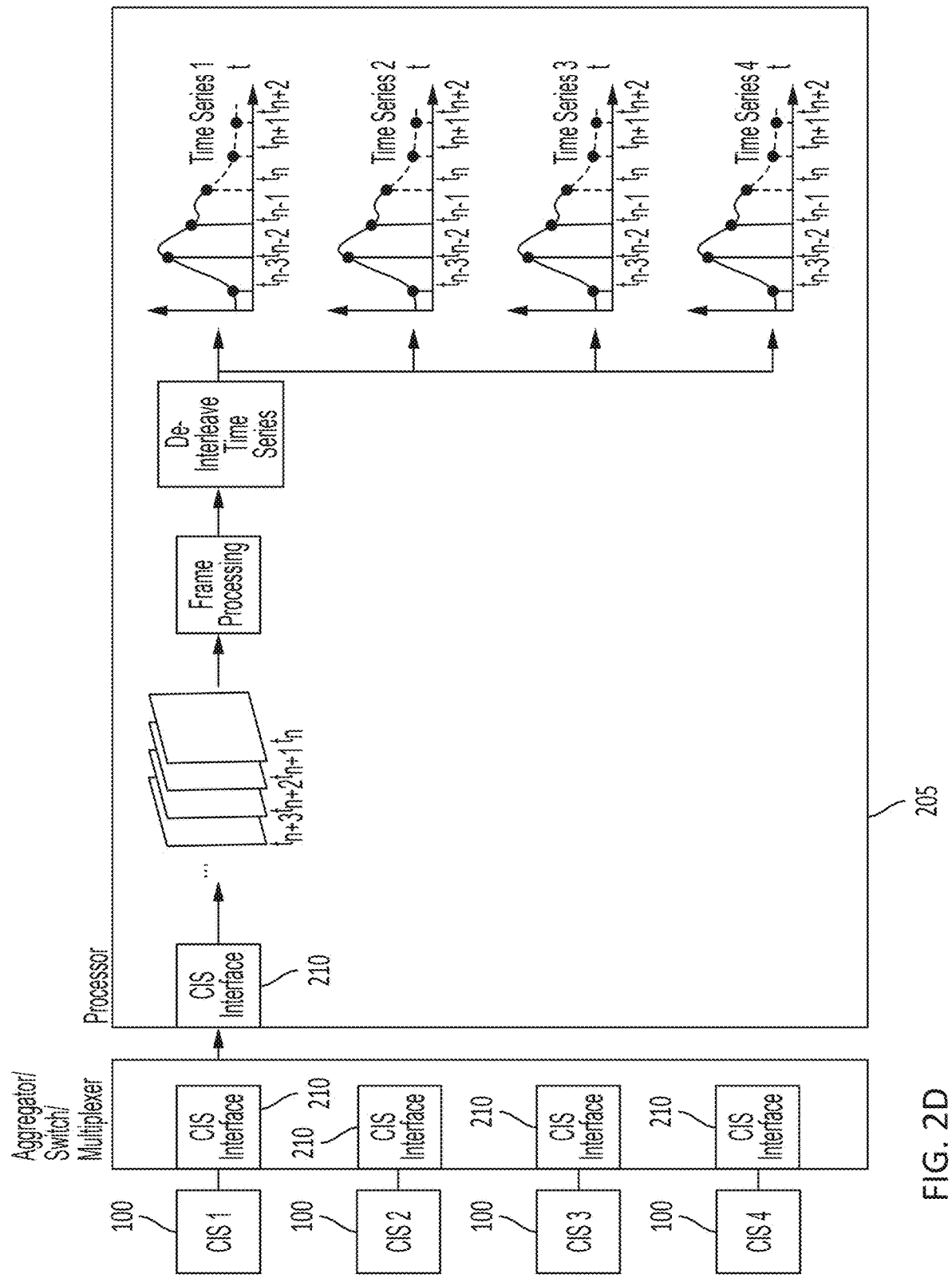
FIG. 2D is a schematic drawing of a plurality of images sensors and processor interfaces, according to an embodiment of the present disclosure.

In some embodiments, e.g., if the processor 205 lacks sufficient processing resources to process the frames in parallel, the frames are processed one at a time (e.g., in series) in the processor 205 (instead of being processed in parallel). In such an implementation, an example of which is shown in FIG. 2D, the frames in the stream provided by the image sensors 100 are processed sequentially and the corresponding data points are de-interleaved to produce a corresponding respective time series for each of the image sensors 100.

In some embodiments, the image sensors 100 are grouped into subsets, and one subset of image sensors 100 is read out at a time, in parallel or in an interleaved manner. For example, after one or more frames have been read from each of a first subset of image sensors 100, the system may switch to reading out a second subset of the image sensors 100, e.g., in an interleaved manner. Once one or more frames have been read from each of the second subset of image sensors 100, the system may switch to a third subset of the image sensors 100, and so on, or it may switch back to the first subset of the image sensors 100.

Figure 3B:
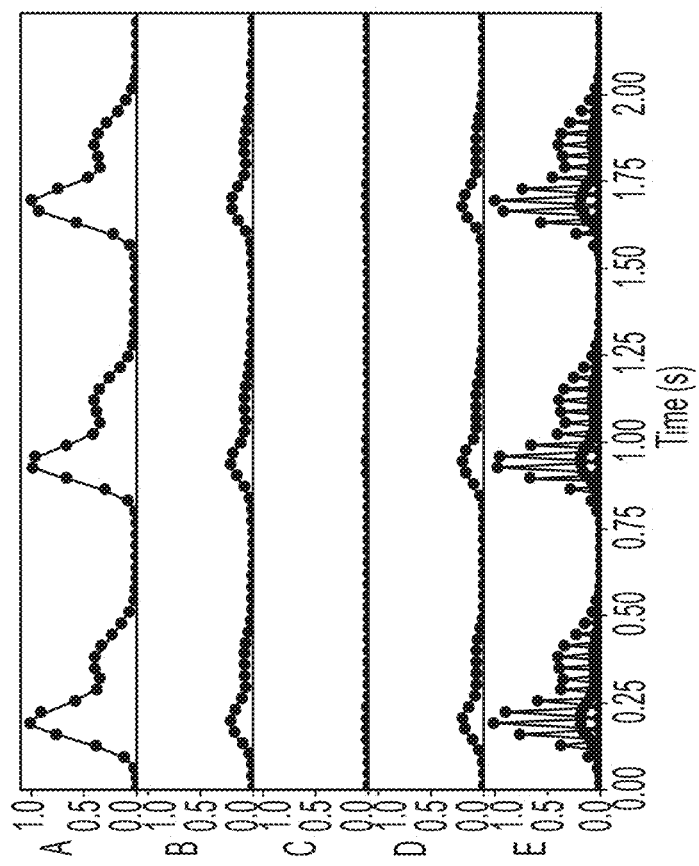
FIG. 3B is a graph of data corresponding to the configuration of FIG. 3A, according to an embodiment of the present disclosure.
Figure 3A:
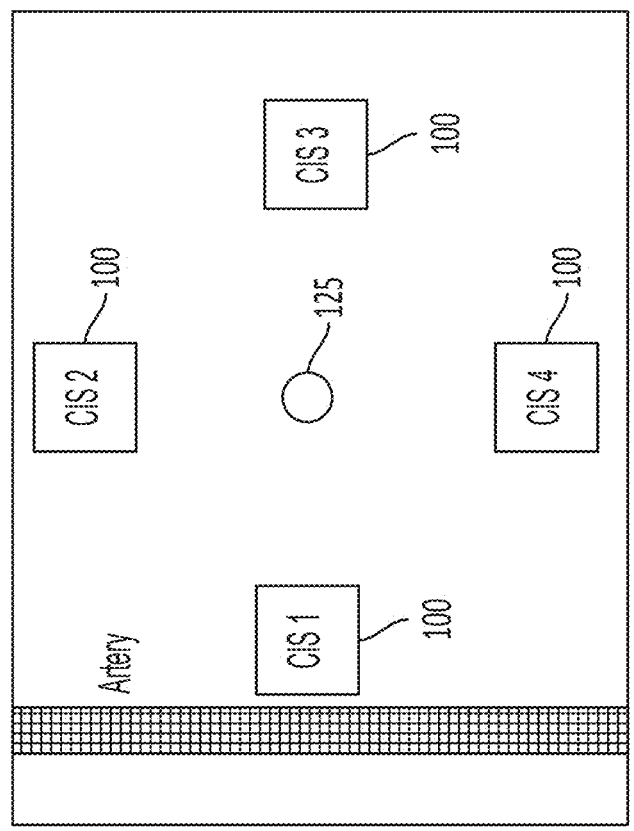
FIG. 3A is a schematic drawing of a sensor with four image sensors, over an artery, according to an embodiment of the present disclosure.

FIG. 3A shows (i) a speckleplethysmography sensor including four image sensors 100 and a single light source 110, and (ii) an artery that is the target of the speckleplethysmography sensor. The resulting representative time series from CIS 1 through 4 are shown in plot A though D respectively, of FIG. 3B; plot E of FIG. 3B shows the composite time series before de-interleaving.

Figure 3C:
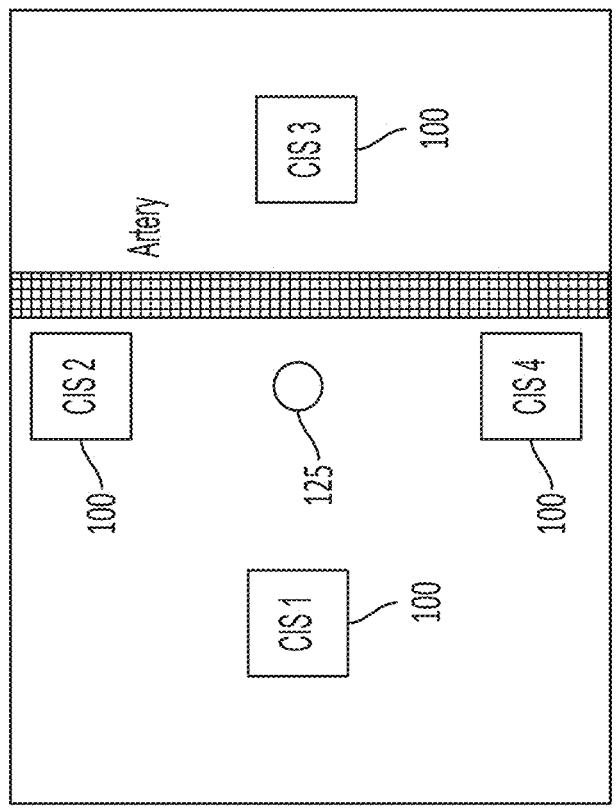
FIG. 3C is a schematic drawing of a sensor with four image sensors, over an artery, according to an embodiment of the present disclosure.
Figure 3D:
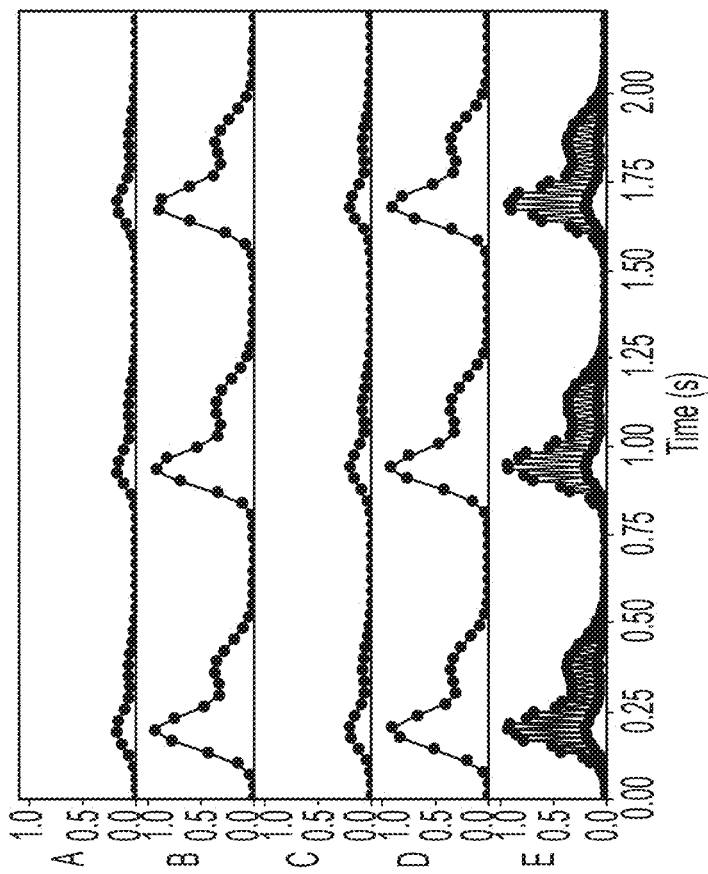
FIG. 3D is a graph of data corresponding to the configuration of FIG. 3C, according to an embodiment of the present disclosure.

FIG. 3C shows the speckleplethysmography sensor of FIG. 3A after the position of the wearable device with respect to the artery has changed (e.g., as a result of a user's moving of the wearable device). The effect on the resulting time series may be seen in the plots in FIG. 3D (in which representative time series from CIS 1 through 4 are shown in plot A though D respectively, and plot E shows the composite time series before de-interleaving); the magnitude of the time series data collected by CIS 2 and 4 is increased in comparison with the times series data corresponding to the position of FIG. 3A.

Figure 4:
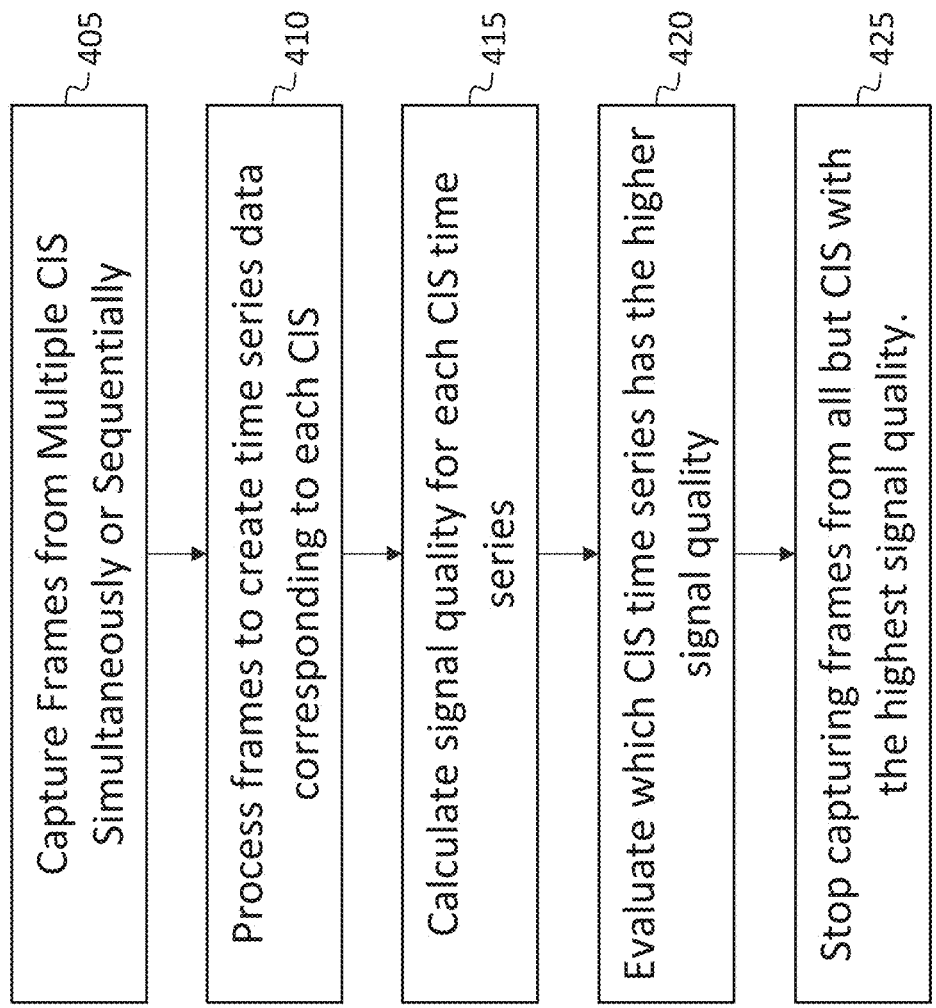
FIG. 4 is a flow chart, according to an embodiment of the present disclosure.

In some embodiments, a speckleplethysmography sensor utilizing multiple image sensors 100 may at startup, or periodically, be operated with all of the image sensors 100 and may then transition to a mode in which only a single image sensor 100 operates, e.g., to conserve power, or to permit the capturing and processing of images at a higher rate. The single image sensor 100 used after the transition may be the image sensor 100 generating the highest signal quality before the transition, where signal quality may be measured by a suitable algorithm (e.g. maximum peak-to-peak amplitude). FIG. 4 shows a flow chart corresponding to such a method. In the method of FIG. 4, frames are captured simultaneously from multiple image sensors 100, at 405; the frames are processed, at 410, to create time series data corresponding to each image sensor 100; the signal quality for each such time series is calculated, at 415; the image sensor 100 producing signals with the highest signal quality is identified, at 420, and the system switches, at 425, to a mode in which it uses only this identified image sensor 100. A transition back to a mode in which all of the image sensors 100 are used may be triggered by an external stimulus (e.g., an accelerometer reading exceeding a threshold) or by a real-time evaluation of the sensor time series data (e.g., peak-to-peak speckle contrast amplitude being below a threshold).

In some embodiments, a difference in signal quality between two image sensors 100 may cause the wearable device to prompt a user to perform an azimuthal adjustment of the wearable device, so as to improve the positioning of the wearable device. For example, in the situation illustrated in FIG. 3A, the system may infer, from the higher signal quality at CIS 1, that an azimuthal displacement of the wearable device, so that the position of the artery is nearer the center of the constellation of image sensors 100, may improve the signal quality at one or more of the image sensors 100, and the wearable device may prompt the user accordingly.

In some embodiments, multiple photodiodes 102, or multiple light sources 110 (e.g., multiple coherent light sources or multiple incoherent light sources) may be used in an analogous manner, to reduce the sensitivity to placement of the wearable device, or to generate information based on which a user may be prompted to adjust the azimuthal position of the wearable device.

In some embodiments with multiple image sensors 100, each image sensor 100 may receive light through a respective separate window in the wearable device (which may be shared with a respective photodiode 102), and a separate window may be used for each light source 110, or for all of the light sources 110.

An image sensor 100 designed for imaging applications may include a micro-lens array that includes one micro-lens for each pixel in the image sensor 100. Each micro-lens may concentrate the received light on the light-sensitive portion of the corresponding pixel (in some devices part of the area of the pixels is allocated to a control and readout circuit and is not light-sensitive). Such a microlens may be offset from the center of the light-sensitive portion of the corresponding pixel if the chief ray angle for the pixel, in an optical system for which the image sensor 100 is intended, is not zero, i.e., if the chief ray corresponding to the pixel is not perpendicular to the plane of the image sensor 100. This may be because the pixel is not near the center of the array (e.g., because the pixel is near the edge of the array). The offsetting of microlenses from the light-sensitive portion of the corresponding pixels may result in vignetting (lower exposure at and near the edges of the image sensor 100) in applications (such as the optodes described herein) in which the illumination is generally diffuse Lambertian illumination, which is approximately isotropic over a large solid angle, because in such a configuration a greater proportion of the received light may miss the light-sensitive portion of the corresponding pixel if the microlens is offset from the light-sensitive portion of the corresponding pixel. As such, in some embodiments, an image sensor 100 that does not include a micro-lens array, or an image sensor 100 that includes a micro-lens array and that is a zero chief ray angle (CRA) image sensor (e.g., an image sensor 100 in which each micro-lens is aligned with (not offset from) the light-sensitive portion of the corresponding pixel) may be used. As used herein, a zero chief ray angle sensor is a sensor (i) that does not include a microlens array or (ii) that includes a micro-lens array in which each chief ray angle is small (e.g., less than 5 degrees) (where the chief ray is a ray that passes through the center of the aperture and ends at the center of the light-sensitive area of the pixel, and the chief ray angle is the angle between the chief ray and a line perpendicular to the plane of the detector 120).

The distance from the sample (e.g., from the skin of the subject) to the image sensor 100 may be less than 5 mm (in a straight line) or less than 15 mm along the optical path (the latter distance being greater than the former if, for example, a folding mirror is used to cause the light from the sample to propagate parallel to the surface of the sample for some distance before reaching the image sensor 100).

The wearable device may be coupled to various other devices and systems which may perform functions of data analysis, data storage, and user interaction. For example, the wearable device may be connected (e.g., via a wireless connection) to a mobile device (such as a mobile telephone or portable (e.g., laptop) computer) and a portion of the data analysis used to convert the signals received from the optical sensors to one or more biomarkers (e.g., blood flow velocity, blood volume, or blood pressure) may be performed in the mobile device. The mobile device may also be connected to the cloud (e.g., to one or more servers connected to the Internet) and data processing and storage may be performed on the cloud. As another example, if an adjustment is to be made (e.g., an adjustment to the azimuthal position of the wearable device), the wearable device may cause the mobile device to give the user a suitable corresponding prompt.

As used herein, "a portion of" something means "at least some of" the thing, and as such may mean less than all of, or all of, the thing. As such, "a portion of" a thing includes the entire thing as a special case, i.e., the entire thing is an example of a portion of the thing. As used herein, when a second quantity is "within Y" of a first quantity X, it means that the second quantity is at least X−Y and the second quantity is at most X+Y. As used herein, when a second number is "within Y %" of a first number, it means that the second number is at least $(1-Y/100)$ times the first number and the second number is at most $(1+Y/100)$ times the first number. As used herein, the word "or" is inclusive, so that, for example, "A or B" means any one of (i) A, (ii) B, and (iii) A and B.

Each of the terms "processing circuit" and "means for processing" is used herein to mean any combination of hardware, firmware, and software, employed to process data or digital signals. Processing circuit hardware may include, for example, application specific integrated circuits (ASICs), general purpose or special purpose central processing units (CPUs), digital signal processors (DSPs), graphics processing units (GPUs), and programmable logic devices such as field programmable gate arrays (FPGAs). In a processing circuit, as used herein, each function is performed either by hardware configured, i.e., hard-wired, to perform that function, or by more general-purpose hardware, such as a CPU, configured to execute instructions stored in a non-transitory storage medium. A processing circuit may be fabricated on a single printed circuit board (PCB) or distributed over several interconnected PCBs. A processing circuit may contain other processing circuits; for example, a processing circuit may include two processing circuits, an FPGA and a CPU, interconnected on a PCB.

As used herein, when a method (e.g., an adjustment) or a first quantity (e.g., a first variable) is referred to as being "based on" a second quantity (e.g., a second variable) it means that the second quantity is an input to the method or influences the first quantity, e.g., the second quantity may be an input (e.g., the only input, or one of several inputs) to a function that calculates the first quantity, or the first quantity may be equal to the second quantity, or the first quantity may be the same as (e.g., stored at the same location or locations in memory as) the second quantity.

The terminology used herein is for the purpose of describing particular embodiments only and is not intended to be limiting of the inventive concept. As used herein, the terms "substantially," "about," and similar terms are used as terms of approximation and not as terms of degree, and are intended to account for the inherent deviations in measured or calculated values that would be recognized by those of ordinary skill in the art.

Any numerical range recited herein is intended to include all sub-ranges of the same numerical precision subsumed within the recited range. For example, a range of "1.0 to 10.0" or "between 1.0 and 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Similarly, a range described as "within 35% of 10" is intended to include all subranges between (and including) the recited minimum value of 6.5 (i.e., $(1-35/100)$ times 10) and the recited maximum value of 13.5 (i.e., $(1+35/100)$ times 10), that is, having a minimum value equal to or greater than 6.5 and a maximum value equal to or less than 13.5, such as, for example, 7.4 to 10.6. Any maximum numerical limitation recited herein is intended to include all lower numerical limitations subsumed therein and any minimum numerical limitation recited in this specification is intended to include all higher numerical limitations subsumed therein.

It will be understood that when an element is referred to as being "directly connected" or "directly coupled" to another element, there are no intervening elements present. As used herein, "generally connected" means connected by an electrical path that may contain arbitrary intervening elements, including intervening elements the presence of which qualitatively changes the behavior of the circuit. As used herein, "connected" means (i) "directly connected" or (ii) connected with intervening elements, the intervening elements being ones (e.g., low-value resistors or inductors, or short sections of transmission line) that do not qualitatively affect the behavior of the circuit.

Although exemplary embodiments of a wearable device with a light source and an optical sensor have been specifically described and illustrated herein, many modifications and variations will be apparent to those skilled in the art. Accordingly, it is to be understood that a wearable device with a light source and an optical sensor constructed according to principles of this disclosure may be embodied other than as specifically described herein. The invention is also defined in the following claims, and equivalents thereof.

What is claimed is:

1. A system, comprising:
    a wearable device for being worn by a subject and for measuring a first biomarker of a blood vessel of the subject,
    the wearable device comprising:
        a first light source, and
        a plurality of optical detectors,
    the system being configured:
        to perform a photoplethysmography measurement with each of the plurality of optical detectors, the first biomarker being a blood volume; or
        to perform a speckleplethysmography measurement with each of the plurality of optical detectors, the first biomarker being a blood flow velocity,
    wherein the wearable device further comprises a receiving window, and the length of an optical path between the receiving window and an optical detector of the plurality of optical detectors is less than 15 mm.

2. The system of claim 1, wherein the system is configured to read interleaved data from the plurality of optical detectors.

3. The system of claim 2, wherein the system is further configured:
    to read first interleaved data from a first subset of the plurality of optical detectors; and
    to read second interleaved data from a second subset of the plurality of optical detectors.

4. The system of claim 1, wherein the system is configured:

to perform a first measurement, with a first optical detector of the plurality of optical detectors;

to perform a second measurement, with a second optical detector of the plurality of optical detectors, the second optical detector being azimuthally separated from the first optical detector; and to determine that a measure of signal quality of the first measurement exceeds a measure of signal quality of the second measurement.

5. The system of claim 4, wherein the system is further configured:

in response to the determining that the measure of signal quality of the first measurement exceeds the measure of signal quality of the second measurement, to perform a third measurement, with the first optical detector.

6. The system of claim 5, wherein:

the system is further configured:

to read first interleaved data from a first subset of the plurality of optical detectors; and to read second interleaved data from a second subset of the plurality of optical detectors, wherein the first optical detector is an optical detector of the first subset, and the second optical detector is an optical detector of the second subset.

7. The system of claim 1, wherein:

the first biomarker is a blood flow velocity, and the plurality of optical detectors comprises a first image sensor and a second image sensor azimuthally separated from the first image sensor.

8. The system of claim 7, wherein the first image sensor is a zero chief ray angle image sensor.

9. The system of claim 8, wherein an optical path between the blood vessel of the subject and the first image sensor includes no lenses.

10. The system of claim 1, wherein the distance between the receiving window and the optical detector is less than 5 mm.

11. The system of claim 1, wherein:

the wearable device further comprises a second light source; and the system is further configured:

to perform a photoplethysmography measurement with the second light source and an optical detector of the plurality of optical detectors; or to perform a speckleplethysmography measurement with the second light source and an optical detector of the plurality of optical detectors.

12. A system, comprising:

a wearable device for being worn by a subject and for measuring a first biomarker of a blood vessel of the subject, the wearable device comprising:

a first light source, and a plurality of optical detectors, the system being configured:

to perform a photoplethysmography measurement with each of the plurality of optical detectors, the first biomarker being a blood volume; or to perform a speckleplethysmography measurement with each of the plurality of optical detectors, the first biomarker being a blood flow velocity wherein the system is configured:

to perform a first measurement, with a first optical detector of the plurality of optical detectors;

to perform a second measurement, with a second optical detector of the plurality of optical detectors, the second optical detector being azimuthally separated from the first optical detector;

to determine that a measure of signal quality of the first measurement exceeds a measure of signal quality of the second measurement;

in response to the determining that the measure of signal quality of the first measurement exceeds the measure of signal quality of the second measurement, to perform a third measurement, with the first optical detector; and in response to the determining that the measure of signal quality of the first measurement exceeds the measure of signal quality of the second measurement, to prompt a user of the system to perform an azimuthal adjustment of the wearable device.

13. A system, comprising:

a wearable device for being worn by a subject and for measuring a first biomarker of a blood vessel of the subject, the wearable device comprising:

a plurality of light sources, and a first optical detector, the system being configured:

to perform a photoplethysmography measurement with each of the plurality of light sources, the first biomarker being a blood volume; or to perform a speckleplethysmography measurement with each of the plurality of light sources, the first biomarker being a blood flow velocity, wherein the system is configured:

to perform a first measurement, with a first light source of the plurality of light sources;

to perform a second measurement, with a second light source of the plurality of light sources, the second light source being azimuthally separated from the first light source;

to determine that a measure of signal quality of the first measurement exceeds a measure of signal quality of the second measurement;

in response to the determining that the measure of signal quality of the first measurement exceeds the measure of signal quality of the second measurement, to perform a third measurement, with the first light source; and in response to the determining that the measure of signal quality of the first measurement exceeds the measure of signal quality of the second measurement, to prompt a user of the system to perform an azimuthal adjustment of the wearable device.

14. The system of claim 13, wherein:

the wearable device further comprises a second optical detector; and the system is further configured:

to perform a photoplethysmography measurement with a light source of the plurality of light sources and the second optical detector; or to perform a speckleplethysmography measurement with a light source of the plurality of light sources and the second optical detector.

* * * * *